United States Patent [19]
Jacobsen et al.

[11] Patent Number: 6,130,340
[45] Date of Patent: Oct. 10, 2000

[54] ASYMMETRIC CYCLOADDITION REACTIONS

[75] Inventors: Eric N. Jacobsen, Boston; Scott E. Schaus, Cambridge, both of Mass.

[73] Assignee: President and Fellows of Harvard College, Cambridge, Mass.

[21] Appl. No.: 09/006,104

[22] Filed: Jan. 13, 1998

[51] Int. Cl.$^7$ ...................... C07D 309/18; C07D 327/06; C07D 335/02
[52] U.S. Cl. .............................. 549/273; 549/18; 549/28; 549/417; 546/25; 546/253
[58] Field of Search ............................... 549/18, 28, 273, 549/419; 546/25, 253

[56] References Cited

U.S. PATENT DOCUMENTS

| | | | |
|---|---|---|---|
| 5,352,814 | 10/1994 | Katsuki et al. | . |
| 5,491,266 | 2/1996 | Babin et al. | . |
| 5,665,890 | 9/1997 | Jacobsen et al. | 549/230 |

FOREIGN PATENT DOCUMENTS

| | | |
|---|---|---|
| 9-67274 | 11/1997 | Japan . |
| 2 304 339 | 3/1997 | United Kingdom . |
| WO 93/03838 | 3/1993 | WIPO . |
| WO 96/21507 | 7/1996 | WIPO . |

OTHER PUBLICATIONS

Evans, et al., "Catalytic Enantioselective Hetero Diels–Alder Reactions of a, B–Unsaturated Acyl Phosphonates with Enol Ethers", *J. Am. Chem. Soc.,* vol. 120, pp. 4895–4896, 1998.

Yao, S., et al., "Catalytic Asymmetric Hetero–Diels—Alder Reactions of Ketones: Chemzymatic Reactions," *American Chemical Society,* 120, pp. 8599–8605, 1998.

Gao, Qingzhi et al., "Asymmetric Hetero Diels–Alder Reaction Catalyzed by Stable and Easily Prepared CAB Catalysts", *Tetrahedron* 4:979–988 (1994).

Johannsen, Mogens, et al., "The first highly enentioselective catalytic hetero–Diels–Alder reaction of ketone", *Chem. Comm.,* 2169–2170 (1997).

Li, L.–S. et al., "Asymmetric hetero–Diels–Alder reaction of 1–alkyl–3silyoxy–1,3–diens with ethyl glyoxate catalyzed by a chiral (salen)colbalt(II) complex", *Tetrahedron: Asymmetry,* 9:2271–2277 (1998).

Schaus, S. et al., "Asymmetric Hetero–Diels–Alder Reactions Catalyzed by Chiral (Salen)Chromium(III) Complexes", *J. Org. Chem.,* 63:403–405 (1998).

Yao, Sulan et al., "Zinc(II)–catalysed asymmetric hetero––Diels–Alder reactions of conjugated dienes with glyoxylate", *J. Chem. Soc., Perkins Trans.,* 1:2345–2349 (1997).

Otto, S., et al., "A Chiral Lewis–Acid–Catalyzed Diels–Alder Reaction. Water–Enhanced Enantioselectivity", *J. Am. Chem. Soc.,* 120, pp. 4238–4239 (1998).

Bednarski, M., et al., "On the Interactivity of Chiral Auxilliaries with Chiral Catalysts in the Hetero Diels–Alder Reaction: A New Route to L–Glycolipids", *American Chemical Society,* 0002–7863/83/1505–6968, (1983).

Bednarski, M., et al., "Mild Lewis Acid Catalysis: Eu(fod)3–Mediated Hetero–Diels–Alder Reaction", *American Chemical Society,* 0002–7863/83/1505–3716, 1983.

Collman, J. P., et al., "Regioselective and Enantioselective Epoxidation Catalyzed by Metalloporphyrins", *Science,* vol. 261, (Sep. 10, 1993).

Corey, E.J., et al., "First Application of Attractive Intramolecular Interactions to the Design of Chiral Catalysts for Highly Enantioselective Diels–Alder Reactions", *J. Am. Chem. Soc.,* 113, 8966–8967, (1991).

Corey, E.J., et al., "Enantioselective Mukaiyama–Aldol and Aldol–Dihydropyrone Annulation Reactions Catalyzed By A Tryptophan–Derived Oxazaborolidine", *Tetrahedron Letters,* vol. 33, No. 46, pp. 6907–6910, (1992).

Danishefsky S.J., et al., "Totally Synthetic Routes to the Higher Monosaccharides", *Angew. Chem. Int. Ed. Engl.* 26, pp. 15–23, (1987).

Gao, Qingzhi, et al., "Asymmetric Hetero Diels–Alder Reaction Catalyzed by Stable and Easily Prepared CAB Catalysts", *J. Org. Chem.,* 57, pp. 1951–1952, (1992).

Ghosh, A.K., et al., "Synthetic Studies Of Antitumor Macrolide Laulimalide: Enantioselective Synthesis Of The C3–C–14 Segment By A Catalytic Hetero Diels–Alder Strategy", *Tetrahedron Letters,* vol. 38, No. 14, pp. 2427–2430 (1997).

Hu, Y.J., et al., "Formal Synthesis of 3–Deoxy–D–manno–2–Octulosonic Acid (KDO) via a Highly Double–Stereoselective Hetero Diels–Alder Reaction Directed by a (Salen) Coll Catalyst and Chiral Diene", *J. Org. Chem.,* vol. 63, pp. 2456–2461, (1998).

Jacobsen, E.N., et al., "Electronic Tuning of Asymmetric Catalysts", *J. Am. Chem. Soc.,* vol. 113, pp. 6703–6704, (1991).

Keck, G.E., et al., "Catalytic Enantioselective Synthesis of Dihydropyrones via Formal Hetero Diels–Alder Reactions of "Danishefshy's Diene" with Aldehydes", *J. Org. Chem.,* vol. 60, pp. 5998–5999, (1995).

Larrow, J.F., et al., "A Practical Method for the Large–Scale Preparation of [N,N–Bis (3,5–di–tert–butylsalicylidene)–1, 2–cyclohexanediaminato (2–)]manganese (III) Chloride, a Highly Enantioselective Epoxidation Catalyst", *J. Org. Chem.,* vol. 59, pp. 1939–1942 (1994).

Larrow, J.R., et al., "Kinetic Resolution of 1,2–Dihydronaphthalene Oxide and Related Epoxides via Asymmetric C–H Hydroxylation", *J. Am. Chem. Soc.,* vol. 116, pp. 12129–12130, (1994).

(List continued on next page.)

*Primary Examiner*—Joseph McKane
*Assistant Examiner*—Taofiq F. Solola
*Attorney, Agent, or Firm*—Matthew P. Vincent; Dana M. Gordon; Foley, Hoag & Eliot LLP

[57] ABSTRACT

The present invention relates to a process for stereoselective cycloaddition reactions which generally comprises a cycloaddition reaction between a pair of chiral or prochiral substrates that contain reactive π-systems, in the present of a non-racemic chiral catalyst, to produce a stereoisomerically enriched product.

69 Claims, No Drawings-

OTHER PUBLICATIONS

Lee, N.H., et al., "Enantiomerically Pure Epoxychromans via Asymmetric Catalysis", *Tetrahedron Letters,* vol. 32, No. 38, pp. 5055–5058, (1991).

Matsukawa, S., et al., "Importance of chiral activators in the asymmetric catalysis of Diels–Alder reactions by chiral titanium (IV) complexes", *Tetrhedron:Aymmetry,* vol. 8, No. 6, pp. 815–816 (1997).

Palucki, M., et al., "Asymmetric Oxidation of Sulfides with H2O2 Catalyzed by (salen) MN (III) Complexes", *Tetrahedron Letters,* vol. 33, No. 47, pp. 7111–7114 (1992).

Sasaki, H., et al., "Rational Design of Mn–Salen Catalyst (2): Highly Enantioselective Epoxidation of Conjugated cis–Olefins", *Tetrahedron,* vol. 50, No. 41, pp. 11827–11838 (1994).

Zhang, W., et al., "Enantioselective Epoxidation of Unfunctionalized Olefins Catalyzed by (Salen) manganese Complexes", *J. Am. Chem. Soc.,* vol. 112, pp. 2801–2803 (1990).

Zhang, W., et al., "Asymmetric Olefin Epoxidation with Sodium Hypochlorite Catalized by Easily Prepared Chiral Mn (III) Salen Complexes", *J. Org. Chem.,* vol. 56, pp. 2296–2298 (1991).

ASYMMETRIC CYCLOADDITION REACTIONS

This invention was supported by NIH Grant No. GM 43214 and the government has certain rights to the invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have some advantages over racemic drug mixtures. These advantages (reviewed in, e.g., Stinson, S. C., *Chem Eng News,* Sept. 28, 1992, pp. 46–79) include fewer side effects and greater potency of enantiomerically pure compounds.

Traditional methods of organic synthesis have often been optimized for the production of racemic materials. The production of enantiomerically pure material has historically been achieved in one of two ways: the use of enantiomerically pure starting materials derived from natural sources (the so-called "chiral pool"); or the resolution of racemic mixtures by classical techniques. Each of these methods has serious drawbacks, however. The chiral pool is limited to compounds found in nature, so only certain structures and configurations are readily available. Resolution of racemates often requires the use of resolving agents; this process may be inconvenient and is certain to be time-consuming. Furthermore, resolution often means that the undesired enantiomer is discarded, thereby wasting half of the material.

Cycloaddition reactions are powerful, frequently-exploited elements of the palette of transformations available to the synthetic organic chemist. There are numerous reasons for the importance of cycloaddition reactions, inter alia: 1) they are concerted reactions; 2) their products are significantly more complex than the required starting materials; 3) the relative simplicity and synthetic accessibility of the required starting materials; and 4) they are capable of generating a number of contiguous stereocenters. The first of these points is tremendously important because concerted reactions transmit to their products in well-understood ways the stereochemical information contained in their starting materials.

The synthetic utility of cycloaddition reactions in which one of the reactants is a carbonyl group or analogue thereof—termed "Hetero"-cycloadditions—has been further expanded by progress in the development of asymmetric catalysts for these reactions. The Hetero-Diels-Alder reaction is perhaps the best example of a cycloaddition reaction whose utility has been has been augmented by research directed at the development of asymmetric catalysts (for a review, see: Danishefsky *Chemtracts: Organic Chemistry* 1989, 273). Catalysts comprising a transition metal ion and a chiral, non-racemic ligand have been reported to render enantioselective various Hetero-Diels-Alder cycloadditions; these reactions gave products in good to excellent enantiomeric excess (for leading references, see: Danishefsky and DeNinno, *Angew. Chim., Intl. Ed. Engl.* 1987, 26, 15–23; Corey and Loh, *J. Am. Chem. Soc.,* 1991, 113 8966–8967; Yamamoto et al., *J. Org. Chem.,* 1992, 57, 1951–1952; Keck et al., *J. Org. Chem.,* 1995, 60, 5998–5999; and Ghosh et al., *Tetrahedron Lett.* 1997, 38, 2427–2430).

The cyclohexene ring generated in a Diels-Alder reaction can be incorporated without further modification into biologically-active natural products, drug candidates, and pharmaceuticals. Additionally, the newly-formed cyclohexene ring may serving as a starting point for further synthetic transformations. For example, the A, B, and C rings of the steroid skeleton are functionalized cyclohexane rings; a number of routes to steriods based on the Diels-Alder reaction have been reported. The olefin in the cyclohexene derived from a Diels-Alder reaction can serve as a functional handle for subsequent transformations. The Diels-Alder reaction tolerates a wide range of "spectator" functionality—functionality not involved in, or affected by, the reaction conditions—which can serve as reactive sites for subsequent transformation. Finally, the so-called Hetero-Diels-Alder reaction provides access to unsaturated six-membered heterocycles.

SUMMARY OF THE INVENTION

In one aspect of the present invention, there is provided a process for enantioselective chemical synthesis which generally comprises reacting a diene and an aldehyde in the presence of a non-racemic chiral catalyst to produce a enantiomerically enriched dihydropyran product. The diene substrate comprises a 1,3-diene moiety, the dienophile comprises a single reactive π-bond, and the chiral catalyst comprises an asymmetric tetradentate or tridentate ligand complexed with a transition metal ion. In the instance of the tetradentate ligand, the catalyst complex has a rectangular planar or rectangular pyrimidal geometry. The tridentate ligand-metal complex assumes a planar geometry. In a preferred embodiment, the ligand has at least one schiff base nitrogen complexed with the metal core of the catalyst. In another preferred embodiment, the ligand provides at least one stereogenic center within two bonds of a ligand atom which coordinates the metal.

In general, the metal atom is a transition metal from Groups 3–12 or from the lanthanide series, and is preferably not in its highest state of oxidation. For example, the metal can be a late transition metal, such as selected from Group 5–12 transition metals. In preferred embodiments, the metal atom is selected from the group consisting of Co, Cr, Mn, V, Fe, Mo, W, Ru and Ni.

Exemplary diene substrates for the subject reaction include 1,3-dienes in which any or all of the heavy atoms comprising the backbone of said 1,3-diene are chosen from the set containing C, N, O, S, and P.

In preferred embodiments, the subject transformation can be represented as follows:

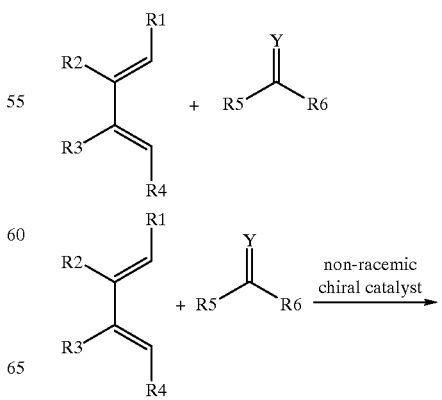

-continued

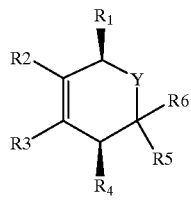

in which

Y represents O, S, or NR$_7$.

For instance, the substituents $R_1$, $R_2$, $R_3$, $R_4$, $R_5$ and $R_6$ each independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyl, carboxyls, silyls, ethers, thioethers, sulfonyls, selenoethers, ketones, aldehydes, esters, or —(CH$_2$)$_m$—R$_8$; or any two or more of the substituents $R_1$, $R_2$, $R_3$, $R_4$, $R_5$ and $R_6$ taken together form a carbocyclic or heterocyclic ring having from 4 to 8 atoms in the ring structure. In this formula, R$_8$ represents an aryl, a cycloalkyl, a cycloalkenyl, a heterocycle or a polycycle; and m is zero or an integer in the range of 1 to 8. In certain embodiments, $R_1$, $R_2$, $R_3$, and $R_4$ are chosen such that the substrate has a plane of symmetry.

Exemplary dienophile substrates for the subject reaction include aldehydes, ketones, esters, amides, carbonates, thioaldehydes, thioamides, thiocarbonates, lactones, lactams, thiollactones, thiolactams, imines, oximes, hydrazones, thionoesters, thioesters, dithioesters, thionolactones, thiolactones, dithiolactones, phosphorus ylides, thioketones, acid halides, anhydrides, imines, iminium ions, imines, oximes, oximes, hydrazones, nitroso-containing compounds, nitro-containing compounds, compounds containing a phosphorus-oxygen π-bond, and compounds containing a phosphorus-sulfur π-bond.

In a preferred embodiment, the method includes combining a diene, a dienophile, and a non-racemic chiral catalyst as described herein, and maintaining the combination under conditions appropriate for the chiral catalyst to catalyze an enantioselective cycloaddition reaction between the two substrates.

In preferred embodiments, the chiral catalyst which is employed in the subject reaction is represented by the general formula:

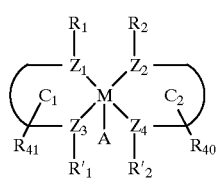

100 in which $Z_1$, $Z_2$, $Z_3$ and $Z_4$ each represent a Lewis base;

the C$_1$ moiety, taken with $Z_1$, $Z_3$ and M, and the C$_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached, $R_{40}$ and $R_{41}$ each independently are absent, or represent one or more covalent substitutions of C$_1$ and C$_2$ with an organic or inorganic substituent permitted by valence requirements of the ring atom to which it is attached, or any two or more of the $R_1$, $R_2$, $R'_1$, $R'_2$ $R_{40}$ and $R_{41}$ taken together form a bridging substituent;

with the proviso that C$_1$ is substituted at at least one site by $R_1$, $R'_1$ or $R_{41}$, and C$_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as a tetradentate;

M represents the late transition metal ion; and

A represents a counterion or a nucleophile, wherein each $R_1$, $R_2$, $R'_1$, $R'_2$ $R_{40}$ and $R_{41}$ are selected to provide at least one stereogenic center in the tetradentate ligand.

In exemplary embodiments, $R_1$, $R_2$, $R'_1$ and $R'_2$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyl, carboxyls, silyls, ethers, thioethers, sulfonyls, selenoethers, ketones, aldehydes, esters, or —(CH$_2$)$_m$—R$_8$;

each $R_{40}$ and $R_{41}$ occurring in 100 independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—R$_8$;

R$_8$ represents an aryl, a cycloalkyl, a cycloalkenyl, a heterocycle or a polycycle;

$Z_1$, $Z_2$, $Z_3$ $Z_4$ are independently selected from the group consisting of nitrogen, oxygen, phosphorus, arsenic, and sulfur; and m is zero or an integer in the range of 1 to 8.

For example, the catalyst can be represented by the general formula:

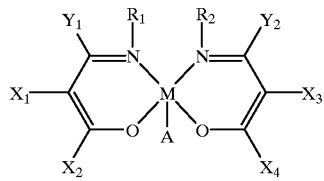

in which the substituents $R_1$, $R_2$, $Y_1$, $Y_2$, $X_1$, $X_2$, $X_3$ $X_4$ each, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—R$_8$, or any two or more of the substituents taken together form a carbocycle or heterocycle ring having from 4 to 8 atoms in the ring structure, with the proviso that at least one of $R_1$, $Y_1$, $X_1$ and $X_2$ is covalently bonded to at least one of $R_2$, $Y_2$, $X_3$ and $X_4$ to provide the β-iminocarbonyls to which they are attached as a tetradentate ligand, and at least one of $Y_1$ and $Y_2$ is a hydrogen;

R$_8$ represents an aryl, a cycloalkyl, a cycloalkenyl, a heterocycle, or a polycycle;

m is zero or an integer in the range of 1 to 8;

M represents the late transition metal; and

A represents a counterion or a nucleophile, wherein each of of the substituents $R_1$, $R_2$, $Y_1$, $Y_2$, $X_1$, $X_2$, $X_3$ and $X_4$, are selected such that the catalyst is asymmetric.

For example, a preferred class of catalysts are represented by the general formula:

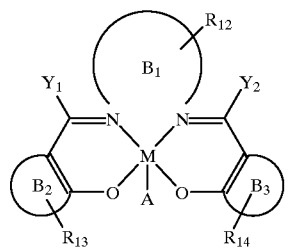

in which the $B_1$ moiety represents a diimine bridging substituent represented by —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphoryl, a carbonyl, a silyl, an oxygen, a sulfur, a sulfonyl, a selenium, a carbonyl, or an ester;

each of $B_2$ and $B_3$ independently represent rings selected from a group consisting of cycloalkyls, cycloalkenyls, aryls, and heterocyclic ring, which rings comprising from 4 to 8 atoms in a ring structure;

$Y_1$ and $Y_2$ each independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_8$, $R_{12}$, $R_{13}$, and $R_{14}$ each independently are absent, or represent one or more covalent substitutions of $B_1$, $B_2$ and $B_3$ with halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_8$, wherein $R_{12}$ can occur on one or more positions of —$R_{15}$—$R_{16}$—$R_{17}$—, or any two or more of the $R_{12}$, $R_{13}$, $R_{14}$, $Y_1$ and $Y_2$ taken together form a bridging substituent;

$R_8$ represents an aryl, a cycloalkyl, a cycloalkenyl, a heterocycle, or a polycycle;

m is zero or an integer in the range of 1 to 8;

M represents a transition metal; and

A represents a counterion or a nucleophile, wherein $R_{12}$, $R_{13}$, $R_{14}$, $Y_1$ and $Y_2$ are selected such that the catalyst is asymmetric.

In yet further preferred embodiments, the catalyst is a metallosalenate catalyst represented by the general formula:

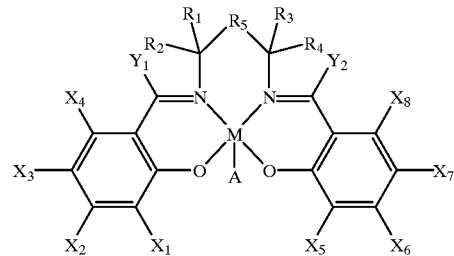

in which each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_8$;

or any two or more of the substituents taken together form a carbocycle or heterocycle having from 4 to 10 atoms in the ring structure;

$R_8$ represents an aryl, a cycloalkyl, a cycloalkenyl, a heterocycle or a polycycle;

m is zero or an integer in the range of 1 to 8;

M represents a transition metal; and

A represents a counterion or a nucleophile;

wherein if $R_5$ is absent, at least one of $R_1$ and $R_2$ is taken together with at least one of $R_3$ and $R_4$ to form a bridging substituent, and each of of the substituents of 106 are selected such that the salenate is asymmetric.

Alternatively, the catalyst can have a tridentate ligand, such as the ligand represented by the general formula:

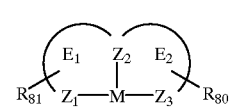

in which $Z_1$, $Z_2$, and $Z_3$ each represent a Lewis base;

the $E_1$ moiety, taken with $Z_1$, $Z_2$ and M, and the $E_2$ moiety, taken with $Z_2$, $Z_3$ and M, each, independently, form a heterocycle;

$R_{80}$ and $R_{81}$ each independently are absent, hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_8$, or any two or more of the $R_{80}$ and $R_{81}$ substituents taken together form a bridging substituent;

$R_8$ represents an aryl, a cycloalkyl, a cycloalkenyl, a heterocycle or a polycycle;

m is zero or an integer in the range of 1 to 8;

M represents a transition metal; and

A represents a counteranion or a nucleophile, wherein the tridentate ligand is asymmetric.

DETAILED DESCRIPTION OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News,* Sept. 28, 1992, pp. 46–79) include fewer side effects and greater potency of enantiomerically pure compounds. As described herein, the present invention makes available methods and reagents for enantioselective synthesis involving cycloaddition reactions. The primary constituents of the method, set out in more detail below, are a chiral, non-racemic metal catalyst of particular tetradentate or tridentate geometry; a chiral or prochiral diene, and a chiral or prochiral dienophile; the diene and/or dienophile are chosen so that the outcome of the reaction is influenced by the presence of the aforementioned chiral, non-racemic catalyst.

I. Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as amines, mercaptans and alcohols, and charged moieties such as alkoxides, thiolates, carbanions, and a variety of organic and inorganic anions. Illustrative anionic nucleophiles include simple anions such as azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like.

The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "diene" refers to a molecule containing at least one pair of conjugated π-bonds. The individual π-bonds of the diene moiety may be between any two atoms drawn from the set composed of C, N, O, S, and P. The conjugated conjugated π-bonds of the diene must be capable of adopting the so-called s-cis conformation.

The term "dienophile" refers to a molecule containing at least one reactive π-bond. The reactive π-bond of the dienophile may be between any two atoms drawn from the set composed of C, N, O, S, and P. In preferred embodiments, exactly one of the atoms contained in the reactive π-bond is carbon.

The term "ring expansion" refers to a process whereby the number of atoms in a ring of a cyclic compound is increased. An illustrative example of ring expansion is the reaction of epoxides with $CO_2$ to yield cyclic carbonates.

The term "meso compound" is recognized in the art and means a chemical compound which has at least two chiral centers but is achiral due to the presence of an internal plane or point of symmetry.

The term "chiral" refers to molecules which have the property of non-superimposability of their mirror image partner, while the term "achiral" refers to molecules which are superimposable on their mirror image partner. A "prochiral molecule" is a molecule which has the potential to be converted to a chiral molecule in a particular process.

The term "steroisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoisomerically-enriched" product (e.g., enantiomerically-enriched or diasteromerically-enriched) when the yield of a particular stereoisomer of the product is greater by a statistically significant amount relative to the yield of that stereoisomer resulting from the same reaction run in the absence of a chiral catalyst. For example, a reaction which routinely produces a racemic mixture will, when catalyzed by one of the subject chiral catalysts, yield an e.e. for a particular enantiomer of the product.

The term "regiosomers" refers to compounds which have the same molecular formula but differ in the connectivity of the atoms. Accordingly, a "regioselective process" is one which favors the production of a particular regioisomer over others, e.g., the reaction produces a statistically significant majority of a certain regioisomer.

The term "reaction product" means a compound which results from the reaction of the two substrate molecules. In general, the term "reaction product" will be used herein to refer to a stable, isolable compound, and not to unstable intermediates or transition states.

The term "complex" as used herein and in the claims means a coordination compound formed by the union of one or more electronically rich molecules or atoms capable of independent existence with one or more electronically poor molecules or atoms, each of which is also capable of independent existence.

The term "substrate" is intended to mean a chemical compound which can react under the subject conditions to yield a product having at least one stereogenic center.

The term "catalytic amount" is recognized in the art and means a substoichiometric amount of the catalyst relative to a reactant. As used herein, a catalytic amount means from 0.0001 to 90 mole percent catalyst relative to a reactant, more preferably from 0.001 to 50 mole percent, still more preferably from 0.01 to 10 mole percent, and even more preferably from 0.1 to 5 mole percent catalyst to reactant.

As discussed more fully below, the reactions contemplated in the present invention include reactions which are enantioselective, disastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

$$\frac{\% \text{ enantiomeric}}{\text{excess } A \ (ee)} = (\% \text{ enantiomer } A) - (\% \text{ enantiomer } B)$$

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a reactant or reactants (which may be achiral, racemic, non-racemic or enantiomerically pure) to a product enriched in one diastereomer. If the chiral reactant is racemic, in the presence of a chiral, non-racemic reagent or catalyst, one reactant enantiomer may react more slowly than the other. This effect is termed a kinetic resolution, wherein the reactant enantiomers are resolved by differential reaction rate to yield an enantiomerically enriched product. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another reactive center. For example, a regioselective cycloaddition reaction of an unsymmetrical 1,3,5-triene substrate would preferentially occur at one of the two 1,3-dienes contained therein.

The term "non-racemic" means a preparation having greater than 50% of a desired stereoisomer, more preferably at least 75%. "Substantially non-racemic" refers to preparations which have greater than 90% ee for a desired stereoisomer, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in it backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, an alkoxyl, a silyloxy, a carbonyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of amines, imines, amides, phosphoryls (including phosphonates and phosphines), sulfonyls (including sulfates and sulfonates), and silyl groups, as well as ethers, thioethers, selenoethers, carbonyls (including ketones, aldehydes, carboxylates, and esters), —$CF_3$, —CN and the like. Exemplary substituted alkyls are described below. Cycloalkyls can be further substituted with alkyls, alkenyls, alkoxyls, thioalkyls, aminoalkyls, carbonyl-substituted alkyls, $CF_3$, CN, and the like.

The terms "alkenyl" and "alkynyl" refer to unsaturated aliphatic groups analogous in length and possible substitution to the alkyls described above, but which contain at least one double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

Thus, the term "alkylamine" as used herein means an alkyl group, as defined above, having a substituted or unsubstituted amine attached thereto. In exemplary embodiments, and "amine" can be represented by the general formula:

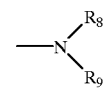

wherein $R_8$ and $R_9$ each independently represent a hydrogen, an alkyl, an alkenyl, —$(CH_2)_m$—$R_7$, —C(=O)-alkyl, —C(=O)-alkenyl, —C(=O)-alkynyl, —C(=O)—$(CH_2)_m$—$R_7$, or $R_8$ and $R_9$ taken together with the N atom to which they are attached complete a heterocycle having from 4 to 8 atoms in the ring structure; $R_7$ represents an aryl, a cycloalkyl, a cycloalkenyl, a heterocycle or a polycycle; and m is zero or an integer in the range of 1 to 8.

Likewise, the term "alkylamide" refers to an alkyl group having a substituted or unsubstituted amide group attached thereto. For instance, an "amide" can be represented by the general formula:

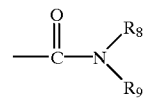

wherein $R_8$ and $R_9$ are as defined above.

The term "alkylimine" refers to an alkyl group having a substituted or unsubstituted imine attached thereto. An "imine" can be represented by the general formula:

wherein $R_8$ is as described above.

The term "thioalkyl" refers to an alkyl group, as defined above, having a sulfhydryl or thioether group attached thereto. In preferred embodiments, the "thioether" moiety is represented by one of —S—alkyl, —S—alkenyl, —S—alkynyl, and —S—$(CH_2)_m$—$R_7$, wherein m and $R_7$ are defined above.

The term "carbonyl-substituted alkyl" as used herein means an alkyl group, as defined above, having a substituted or unsubstituted carbonyl group attached thereto, and includes aldehydes, ketones, carboxylates and esters. In exemplary embodiments, the "carbonyl" moiety is represented by the general formula:

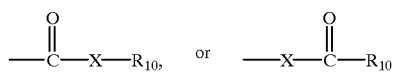

wherein X is absent or represents an oxygen or a sulfur, and $R_{10}$ represents a hydrogen, an alkyl, an alkenyl, or —$(CH_2)_m$—$R_7$, where m and $R_7$ are as defined above. Where X is an oxygen, the formula represents an "ester". Where X is a sulfur, the formula represents a "thioester." Where X is absent, and $R_{10}$ is not hydrogen, the above formula represents a "ketone" group. Where the oxygen atom of the above formula is replaced by sulfur, the formula represents a "thiocarbonyl" group.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl which renders that alkyl an ether is or resembles an alkoxyl, such as can be represented by one of —O—alkyl, —O—alkenyl, —O—alkynyl, —O—$(CH_2)_m$—$R_7$, where m and $R_7$ are described above.

Thus, the term "phosphorylalkyl" as used herein means an alkyl group, as defined above, having a substituted or unsubstituted phosphoryl group attached thereto. A "phosphoryl" can in general be represented by the formula:

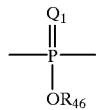

wherein $Q_1$ represented S or O, and $R_{46}$ represents hydrogen, a lower alkyl or an aryl. When used to substitute an alkyl, the phosphoryl group of the phosphorylalkyl can be represented by the general formula:

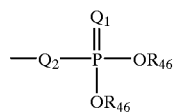

wherein $Q_1$ represented S or O, and each $R_{46}$ independently represents hydrogen, a lower alkyl or an aryl, $Q_2$ represents O, S or N.

The term "metalloalkyl" refers to an alkyl group, as defined above, having a substituted or unsubstituted organometallic group attached thereto. A "silyl alkyl" is an alkyl having a substituted silicon attached thereto. In a preferred embodiment, the "silyl" moiety which may be substituted on the alkyl can be represented by the general formula:

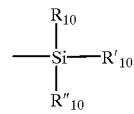

wherein $R_{10}$, $R'_{10}$ and $R''_{10}$ independently represent a hydrogen, an alkyl, an alkenyl, or —$(CH_2)_m$—$R_7$, m and $R_7$ being defined above.

Likewise, a "selenoalkyl" refers to an alkyl group having a substituted seleno group attached thereto. Exemplary "selenoethers" which may be substituted on the alkyl are selected from one of —Se—alkyl, —Se—alkenyl, —Se—alkynyl, and —Se—$(CH_2)_m$—$R_7$, m and $R_7$ being defined above.

The term "sulfonate" as used herein means a sulfonyl group, as defined above, attached to an alkyl or aryl group. Thus, in a preferred embodiment, a sulfonate has the structure:

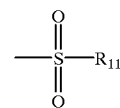

in which $R_{11}$ is an alkyl or an aryl.

The term sulfate, as used herein, means a sulfonyl group, as defined above, attached to a hydroxy or alkoxy group. Thus, in a preferred embodiment, a sulfate has the structure:

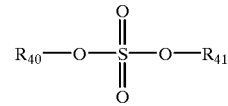

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —$CN$, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —$CN$, or the like.

The term "heteroatom" as used herein means an atom of any element other than carbon or hydrogen. Preferred heteroatoms are nitrogen, oxygen, sulfur, phosphorus and selenium.

A "bridging substituent" refers to a substitution at two (or more) sites on the core structure of the catalyst by the same (as opposed to identical) substituent so as to form a covalent bridge between the substitution sites. For example, a bridging substituent may be represented by the general formula or —$R_{15}$—$R_{16}$—$R_{17}$—, wherein $R_{15}$ and $R_{17}$ each independently are absent or represent an alkyl, an alkenyl, or an alkynyl, preferably $C_1$ to $C_{10}$, and $R_{16}$ is absent or represents an amine, an imine, an amide, a phosphoryl a carbonyl, a silyl, an oxygen, a sulfonyl, a sulfur, a selenium, or an ester. Exemplary bridging substituents are given by the "picnic basket" forms of, for instance, the porphoryn catalysts described below.

For purposes of this invention, the chemical elements are identified in accordance with the Periodic Table of the Elements, CAS version, Handbook of Chemistry and Physics, 67th Ed., 1986–87; inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted and unsubstituted.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

II. Catalyzed Reactions

In one aspect of the present invention there is provided a process for stereoselectively producing compounds with at least one stereogenic center. An advantage of this invention is that enantiomerically enriched products can be synthesized from achiral or racemic reactants. Another advantage is that yield losses associated with the production of an undesired enantiomer can be substantially reduced.

In general, the invention features a stereoselective cycloaddition process which comprises combining a diene, a dienophile, and at least a catalytic amount of a non-racemic, chiral catalyst of particular characteristics (as described below). The combination is maintained under conditions appropriate for the chiral catalyst to catalyze stereoselective cycloaddition between the diene and dienophile. This reaction can be applied to enatioselective processes as well as diastereoselective processes. It may also be adapted for regioselective reactions. Examples of enantioselective reactions, kinetic resolution, and regioselective reactions which may be catalyzed according to the present invention follow.

In an exemplary embodiment, a Hetero-Diels-Alder reaction between an aldehyde and an electron-rich diene in the presence of a subject chiral, non-racemic catalyst yields a non-racemic dihydropyran product. This embodiment is an example of a diastereo- and enantioselective cycloaddition reaction.

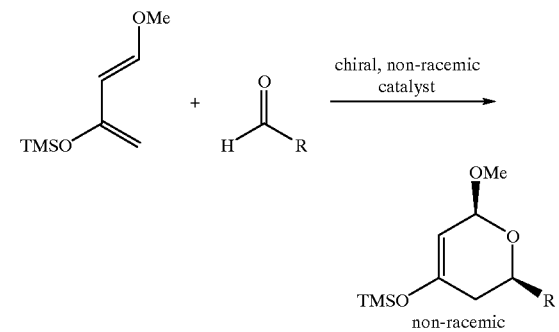

In another aspect of the invention, the hetero-Diels-Alder reaction occurs in a regioselective manner in the presence of a chiral, non-racemic catalyst. An illustrative example of a regioselective reaction is shown below. This exemplary embodiment of the subject invention involves diastereo-, regio- and enantioselective Hetero-Diels-Alder reactions exemplified by the thiene synthesis below.

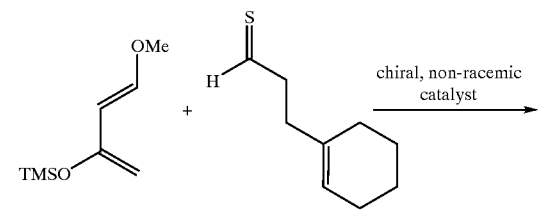

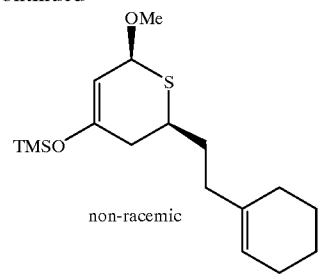

non-racemic

As shown below, the present invention also provides a method for stereoselective type 1 and type 2 intramolecular Hetero-Diels-Alder reactions.

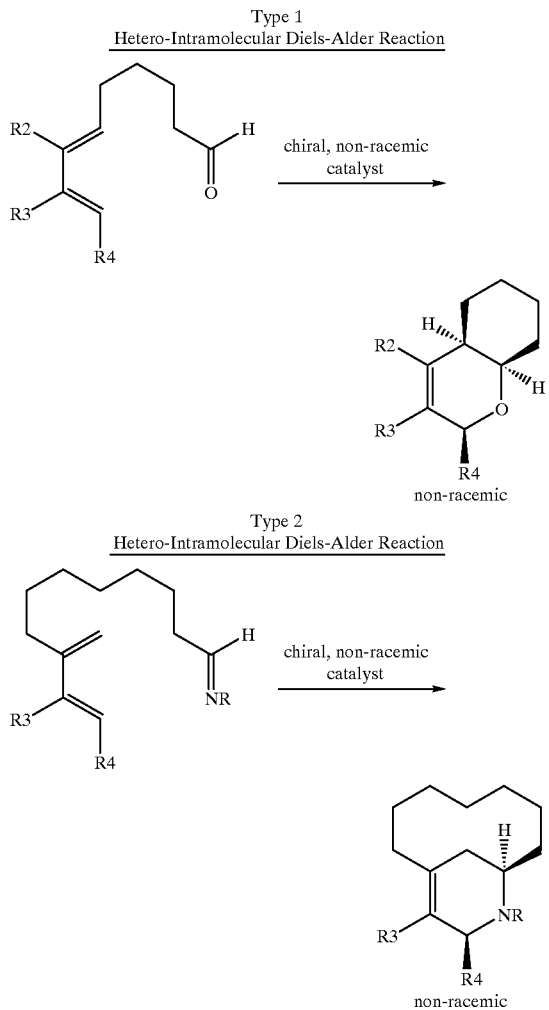

In another illustrative embodiment, the present invention provides a method for the kinetic resolution of a racemic mixture of an aldehyde containing an α-stereocenter. In the subject metal-mediated kinetic resolution process of a racemic aldehyde substrate, one enantiomer of the aldehyde can be recovered as unreacted substrate while the other is transformed to the desired product. This aspect of the invention provides methods of easily synthesizing funtionalized non-racemic products from racemic starting materials.

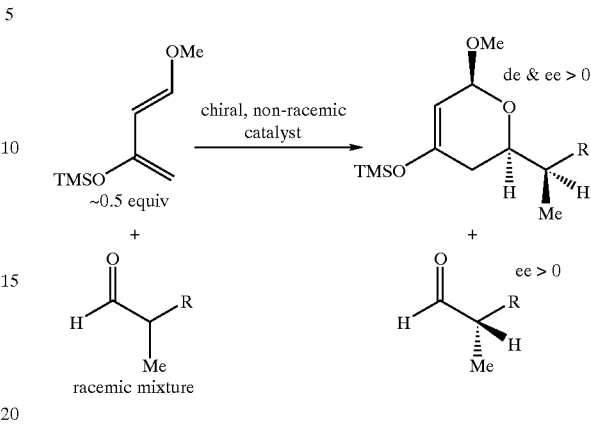

A second facet of kinetic resolution possible with the subject method involves resolution of a racemic diene substrate. In a preferred embodiment, racemic diene A will react with substoichiometric benzaldehyde (~0.5 equiv) in the presence of a subject chiral, non-racemic catalyst to yield dihydropyran B (de and ee>0) and unreacted A(ee>0). This type of kinetic resolution is rationalized by a presumed difference in the energies of the diastereomeric transition states for the reaction between the individual enantiomers of racemic A, and the chiral, non-racemic complex comprising benzaldehyde and the catalyst. This rationalization is not intended to be limiting in any way.

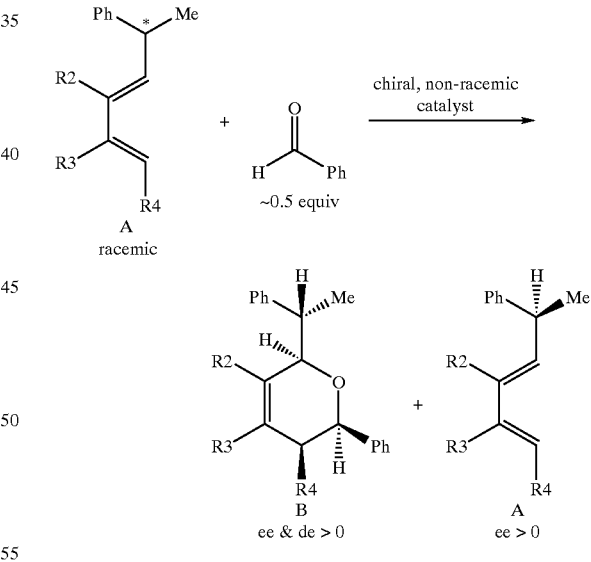

As skilled artisans will recognize readily, the subject invention can be applied to 1,3-dienes which incorporate heteroatoms in their diene backbones. In a preferred embodiment, the 2-aza-1,3-diene shown below will react with acetaldehyde in the presence of a subject catalyst to provide stereoselectively the heterocyclic product.

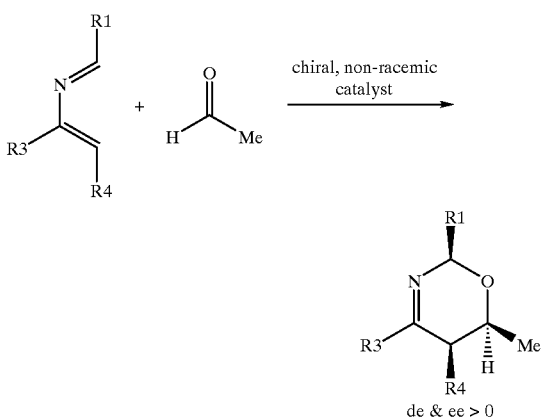

The overall reaction of an aldehyde with a 1,3-diene to generate a dihydropyran—the "classical" diene-aldehyde cyclocondensation reaction—has been shown to proceed via a stepwise, rather than a concerted, mechanism in certain cases (refer to the articles by Corey and Keck cited earlier for relevant examples and a discussion of this issue). Based on this prior art, a preferred embodiment of the present invention involves the use of the instant chiral, non-racemic catalysts for the asymmetric aldol condensation of an aldehyde and a silyl enol ether. In additional preferred embodiments, the aldehyde substrate for these so-called "Mukaiyama" aldol condensations may be replaced with any carbonyl-containing compound including, but not limited to, ketones, ester, amides, imines and the like.

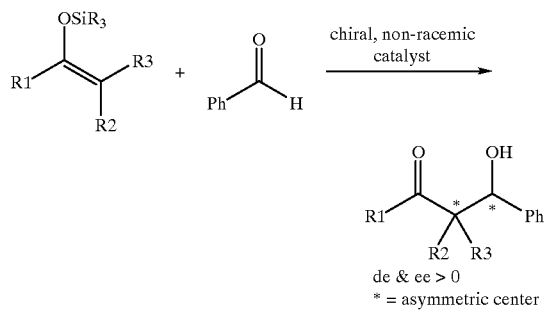

The processes of this invention can provide optically active products with very high stereoselectivity (e.g., enantioselectivity or diastereoselectivity) or regioselectivity. In preferred embodiments of the subject enantioselective reactions, enantiomeric excesses of preferably greater than 50%, more preferably greater than 75% and most preferably greater than 90% can be obtained by the processes of this invention. Likewise, with respect to regioselective reactions, molar ratios for desired/undesired regioisomers of preferably greater than 5:1, more preferably greater than 10:1 and most preferably greater than 25:1 can be obtained by the processes of this invention. The processes of this invention can also be carried out at highly desirable reaction rates suitable for commercial use.

As is clear from the above discussion, the chiral products produced by the asymmetric synthesis processes of this invention can undergo further reactions(s) to afford desired derivatives thereof. Such permissible derivatization reactions can be carried out in accordance with conventional procedures known in the art. For example, potential derivatization reactions include epoxidation, ozonolysis, halogenation, hydrohalogenation, hydrogenation, esterification, oxidation of alcohols to aldehydes, ketones and/or carboxylate derivatives, N-alkylation of amides, addition of aldehydes to amides, nitrile reduction, acylation of alcohols by esters, acylation of amines and the like. To further illustrate, exemplary classes of pharmaceuticals which can be synthesized by a scheme including the subject stereoselective reaction are cardiovascular drugs, nonsteroidal antiinflammatory drugs, central nervous system agents, and antihistaminics.

III. Catalysts

The catalysts employed in the subject method involve chiral complexes which provide controlled steric environments for asymmetric cycloaddition reactions. In general, catalysts intended by the present invention can be characterized in terms of a number of features. For instance, a salient aspect of each of the catalysts contemplated by the instant invention concerns the use of metalloligands which provide a rigid or semi-rigid environment near the catalytic site of the molecule. This feature, through imposition of structural rigidity on the chelated metal, can be used to establish selective approach of the substrate to the catalytic site and thereby induce stereoselectivity and/or regioselectivity in a cycloaddition reaction. Moreover, the ligand preferably places a restriction on the coordination sphere of the metal.

Another aspect of the catalyst concerns the selection of metal atoms for the catalyst. In general, any transition metal (e.g., having d electrons) may be used to form the catalyst, e.g., a metal selected from one of Groups 3–12 of the periodic table or from the lanthanide series. However, in preferred embodiments, the metal will be selected from the group of late transition metals, e.g. preferably from Groups 5–12, in order to provide metal centers which are coordinatively unsaturated and not in their highest oxidation state. For example, suitable metals include Co, Cr, Mn, V, Fe, Mo, W, Ru and Ni. Particularly preferred metals are from group 6, especially Cr(III).

A. Chiral Tetradentate Catalysts

Consistent with these desirable features, one class of particularly preferred chiral catalysts provide a chiral tetradentate ligand which coordinates a transition metal in a substantially square planar or square pyramidal geometry, though some distortion to these geometries is contemplated. Restated, these square geometries refer to tetradentate ligands in which the Lewis basic atoms lie substantially in the same plane, with the metal also in that plane (square planar), or above or below that plane (square pyramidal).

Preferred square tetradentate catalysts which may be employed in the subject reactions can be represented by the general formula 100:

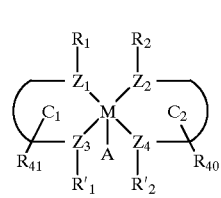

wherein $Z_1$, $Z_2$, $Z_3$ and $Z_4$ each represent a Lewis base, such as selected from the group consisting of nitrogen (e.g., imines, amines and amides), oxygen, phosphorus (e.g., phosphines or phosphinites), arsenic (arsines) and sulfur.

The $C_1$ moiety (taken with $Z_1$, $Z_3$ and M) and the $C_2$ moiety, (taken with $Z_2$, $Z_4$ and M) each, independently, form a heterocyclic ring. It will be understood that while the $C_1$ and $C_2$ structures depicted in the above formula may not formally be covalently closed rings for lack of a covalent bond with the metal M, for purposes of this disclosure, this and similar structures involving the metal catalyst atom M will nevertheless be referred to as heterocyclic rings, and substituents thereof will be referenced relative to heterocycle nomenclature (e.g. "fused rings" or "bridged rings"). In addition to substitutions at $R_1$, $R_2$, $R'_1$ and $R'_2$, the $C_1$ and $C_2$ rings can of course be substituted as appropriate at other ring positions, as illustrated by $R_{40}$ and $R_{41}$. Moreover, it will be appreciated that in certain embodiments two or more substituents of $C_1$ can be covalently bonded to each other to provide a fused ring or bridged ring including the $C_1$ ring atoms. Similar structures can be provided on the $C_2$ ring.

Accordingly, in the illustrated structure 100, $R_1$, $R_2$, $R'_1$ and $R'_2$ each independently are absent, or represent some substitution, as permitted by valence requirements, of the Lewis basic atoms, which substitution may be with hydrogen, halogens, alkyls, alkenyls, alkynyls, hydroxyl, alkoxyl, silyloxy, amino, nitro, thio amines, imines, amides, phosphonates, phosphonates, phosphines, carbonyls, carboxyls, silyls, ethers, thioethers, sulfonyls, selenoethers, ketones, aldehydes, esters, or —$(CH_2)_m$—$R_7$, $R_{40}$ and $R_{41}$ each independently are absent, or represent one or more covalent substitutions of $C_1$ and $C_2$ with an organic or inorganic substituent permitted by valence requirements of the ring atom to which it is attached, or any tow or more of the $R_1$, $R_2$, $R'_1$, $R'_2$ $R_{40}$ and $R_{41}$ substituents taken together can form a bridging substituent; with the proviso that at least one of $R_1$, $R'_1$ and $R_{41}$ forms a bridging substituent with at least one of $R_2$, $R'_2$ and $R_{40}$ in order to provide $C_1$ and $C_2$ as a tetradentate; $R_7$ represents an aryl, a cycloalkyl, a cycloalkenyl, a heterocycle or a polycycle, and m is zero or an integer in the range of 1 to 8.

While the actual substituents of $C_1$ and $C_2$ can vary widely as necessary for a particular reaction scheme, one important proviso is that at least one substituent of $C_1$ must form a covalent bond with at least one substituent of $C_2$ in order to provide a tetradentate ligand which forms a square complex with M. That is, the ligand is a bridged cycle or polycycle which includes $C_1$ and $C_2$. Furthermore, in order for the catalyst to be chiral, e.g., to be capable of catalyzing stereoselective reactions, $R_1$, $R_2$, $R'_1R'_2$ and other substituents of $C_1$ and $C_2$ are selected to provide at least one stereogenic center or an axis of dissymmetry, e.g. such that the ligand is asymmetric.

In the general structure 100, M represents a transition metal of Group 3–12 or the lanthide series of the periodic table, though preferably a metal ion which is not in its highest oxidation state. In the most preferred embodiments, M will be selected from the group of late transition metals, e.g., from the Group 5–12 metals. Even more preferably, M will be Cr(III). Moreover, the metal can be coordinated with a counteranion or a nucleophile (as in the aged catalyst described below).

Exemplary catalysts of this class are comprised of ligands derived from, for example, salens, porphyrins, crown ethers, azacrown ethers, cyclams, phthalocyanines, and the like.

In a particularly preferred embodiment, the subject reactions use a chiral catalyst having a metal ion complexed via an imine of a chiral ligand, preferably a diimine bridge. Accordingly, such variants of structure 100 can be provided in embodiments wherein any one or more of the Lewis bases is an imine, with metallo-schiff base forms of imines being highly preferred.

To further illustrate, a tetradentate catalyst useful in the subject method can be derived using chiral salen or salen-like ligands (hereinafter "salenates"). The asymmetric metallosalenate catalysts offer a distinct advantage over many other chiral tetradentate catalysts, such as the metalloporphyrinates described infra, in that the salenate ligand can have stereogenic centers located just two bond lengths away from the metal. This proximity of the chiral centers to the reactive site can yield a high degree of stereoselectivity.

As disclosed herein, salen complexes are highly effective catalysts for the asymmetric heterO-Diels-Aldser reaction and other cycloaddition reactions. This group of reactions is notable not only for its high enantioselectivity and for the utility of its products, but also for its remarkable efficiency as a catalytic process.

Moreover, the synthesis of chiral salenates is well characterized in the art, with more than 150 different chiral metallosalenates having been reported in the literature (see, for review, Collman et al. (1993) *Science* 261:1404–1411). These ligands are easily and inexpensively synthesized on large scale starting from readily available materials, as described in Larrow et al., *J Org Chem* (1994) 59:1939–1942. Importantly, the general familiarity and ease of synthesis of metallosalenates permits the substituents to be readily varied in a systematic fashion in order to adjust the steric or electronic characteristics of the ligand. This feature makes possible the synthesis of ligands which are optimized for particular types of reaction or substrate. It has been found that such steric and electronic "tuning" (described infra) can have significant effects on the yield and e.e. of products formed in asymmetric reactions. In particular, the use of bulky blocking substituents is desirable to achieve high product e.e. in the asymmetric cycloadditions. Furthermore, the stereogenic moiety can easily be modified to improve enantioselectivity.

In general, the salenate ligands which are useful in the subject method as chiral metallosalenate catalysts can be characterized as two substituted β-iminocarbonyls which are linked to form a tetradentate ligand having at least one stereogenic center. In an exemplary embodiment, a metallosalenate catalyst useful in the asymmetric cycloaddition processes of the present invention can be represented by a metal complex with two substituted β-iminocarbonyls having the general formula:

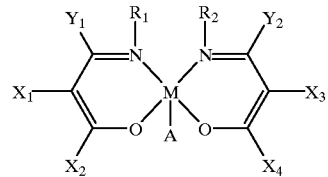

in which
the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$-$R_7$,
or any two or more of the substituents taken together form a carbocycle or heterocycle having from 4 to 8 atoms in the ring structure, which ring structure may be a fused ring, as in the case of, for example, $X_1$ and $X_2$ forming a ring, or which ring may be a bridging ring, as in the case of $R_1$ and $R_2$, $X_2$ and $X_4$, or $Y_1$ and $X_2$ representing different ends of a single substituent, with the proviso that at least one of $R_1$, $Y_1$, $X_1$ and $X_2$ is covalently bonded to at least on of $R_2$, $Y_2$, $X_3$ and $X_4$ to provide the β-iminocarbonyls as a tetradentate ligand;

$R_7$ represents an aryl, a cycloalkyl, a cycloalkenyl, a heterocycle, or a polycycle;

m is zero or an integer in the range of 1 to 8;

M represents a transition metal; and

A represents a counterion or a nucleophile;

wherein each of the substituents of the β-iminocarbonyls, e.g., $R_1$, $R_2$, $Y_1$, $Y_2$, $X_1$, $X_2$, $X_3$ and $X_4$, are selected such that the catalyst is asymmetric.

The choice of each of $R_1$, $R_2$, $Y_1$, $Y_2$, $X_1$, $X_2$, $X_3$ and $X_4$ is also dependent on electronic and steric considerations, e.g., the tuning of the catalyst for a particular set of substrates, as well as the solvent system in which the reaction is to be carried out.

The chirality of the salenate ligand may be the result of the present of one or more chiral atoms (e.g. carbon, sulfur, phosphorus, or other atoms capable of chirality), or may be the result of an axis of asymmetry due to restricted rotation, helicity, molecular knotting or chiral metal complexation. In preferred embodiments, the chiral ligand has at least one chiral atom or axis of asymmetry due to restricted rotation. Further guidance respecting the particular choice of the substituents is set out herein.

In preferred embodiments, the choice of $R_1$, $R_2$, $X_1$, $X_2$, $X_3$ and $X_4$ yield a class of chiral catalysts which are represented by the general formula:

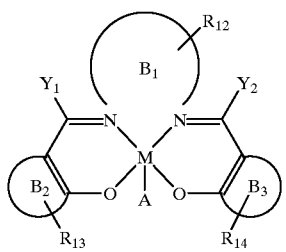

104 in which the $B_1$ moiety represents a diimine bridge, e.g. a bridging substituent which links the imino nitrogens of each β-iminocarbonyl, and preferably contains at least one chiral center of the salen ligand. For example, $B_1$, taken together with the metal-coordinating imines of the β-iminocarbonyl, can represent the diimine of an alkyl, an alkenyl, an alkynyl, or the diimine of $-R_{13}-R_{16}-R_{17}-$, wherein $R_{15}$ and $R_{17}$ each independently are absent or represent an alky, an alkenyl, or an alkynyl, and $R_{16}$ is absent or represents an amine, an imine, an amide, a phosphonate, a phosphine, a carbonyl, a carboxyl, a silyl, an oxygen, a sulfur, a sulfonyl, a selenium, or an ester; each $B_2$ and $B_3$ independently represent rings selected from a group consisting of cycloalkyls, cycloalkenyls, aryls, and heterocycles, which rings comprise from 4 to 8 atoms in a ring structure. The substituents $R_{12}$, $R_{13}$ and $R_{14}$ each independently are absent, or represent one or more covalent substitutions of $B_1$, $B_2$ and $B_3$ with halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or $-(CH_2)_m-R_7$ (the substituent $R_{12}$ occurring on one or more positions of $-R_{15}-R_{16}-R_{17}-$); $R_7$ represents an aryl, a cycloalkyl, a cycloalkenyl, a heterocycle, or a polycycle; m is zero or an integer in the range of 1 to 8. Moreover, any two or more of the $R_{12}$, $R_{13}$, $R_{14}$, $Y_1$ and $Y_2$ substituted taken together can form bridging substituents to bridge the two β-iminocarbonyls and/or bridge different portions of the same β-iminocarbonyl. As above, in order to provide for a chiral catalyst, the choice of $B_2$ and $B_3$ (including their substituents) and/or the choice of substituents of $B_1$ (e.g., $B_1$ has a stereogenic center) is made to establish a chiral ligand. A represents a counterion.

In particular, as described in the appended examples, the salenate ligand can be derived from condensation of a substituted salicylaldehyde with a substituted diamine, preferably one stereoisomer of a chiral diamine, and then reacted with a desired metal to form a salen (N,N'-bis (salicylideneamino)alkyl) metal complex. An exemplary reaction for generating the salen ligand is based on Zhang and Jacobsen (1991) *J Org Chem* 56:2296–2298, and Jacobsen et al. PCT WO93/03838, and comprises:

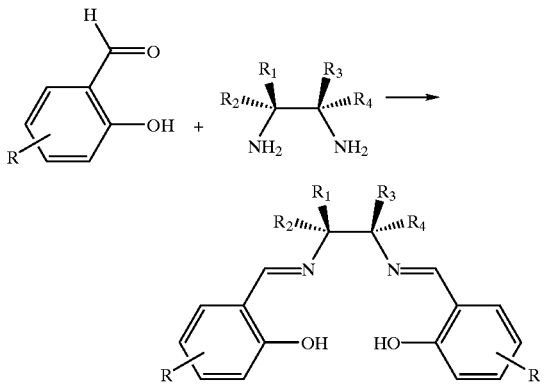

Utilizing this and other reaction schemes generally known in the art can provide a class of salens represented by the general formula:

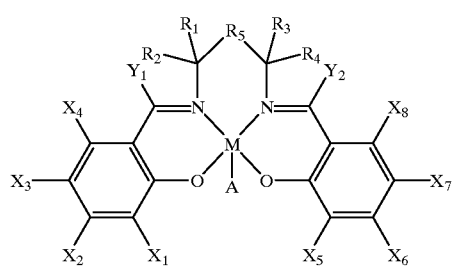

106 in which
each of the substituents $R_1R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyl, selenoethers, ketones, aldehydes, esters, or $-(CH_2)_m-R_7$;

or any two or more of the substituents taken together form a carbocycle of heterocycle having at least 4 atoms in the ring structure;

$R_7$ represents an aryl, a cycloalkyl, a cycloalkyl, a cycloalkenyl, a heterocycle or a polycycle;

m is zero or an integer in the range of 1 to 8; and

M represents a transition metal;

wherein if $R_5$ is absent, at least one of $R_1$ and $R_2$ is covalently bonded to at least one of $R_3$ and $R_4$; and the substituents of the salenate ligand are selected such that the salenate has at least one stereogenic center, e.g., is asymmetric. Moreover, the metal can be coordinated with a counterion (as in the aged catalyst described below).

With respect to generating a chiral ligand, it is important to note when selecting particular substituents that the salenate ligand has a potential catalytic site on both "sides" of the catalyst, e.g., relative to the plane of the four coordinating atoms of the ligand. Accordingly, when selecting the appropriate substituents for the β-iminocarbonyls in the above embodiments, it is important that either (1) both sides of the catalyst have stereogenic centers which effect identical stereoselectivity, or (2) the side having a stereogenic center of appropriate stereoselectivity is accessible while the other side has a blocking structure which substantially impairs substrate approach to the metal atom on that side.

The first of these options is preferred. In other words, it is preferred to have at least one stereogenic center on each side of the salenate ligand, each having the same R/S configuration. For example, (R,R)-1,2-Diphenyl-1,2-bis(3-tert-butylsalicylideamino)ethane, described in Example 1, contains two stereogenic centers on the diimine bridge which give rise to identical stereoselective faces on each side of the catalyst. This bis-faced catalyst has the advantage of not being susceptible to "leakage" reactions because substrate approach, albeit constrained, may occur from either face without loss of selectivity.

In contrast, control of the reactivity of the mono-faced catalyst can be accomplished by sterically hindering substrate approach to the undesired face. For instance, the salenate (R)-2-phenyl-1,2-bis(3-tert-butylsalicylideamino) ethane, e.g., formula 106 wherein $R_1$, $R_2$ and $R_3$ are protons, and $R_4$ is a phenyl, has two non-equivalent faces in terms of enantioselectivity. Accordingly, derivatizing the salenate ligand with a group which blocks access to the "free" face (e.g., the face having both a C1 and C2 proton of the diimine) can establish the ligand as a chiral catalyst with one enantiotopic face. For instance, a "picnic basket" form of the ligand can be generated wherein the phenyl moiety of the diimine bridge is on the "frontside" of the catalyst, and $X_4$ and $X_8$ are covalently linked to form a bridge on the "backside" of the catalyst, which bridge substitution precludes access to the metal ion from the backside. Those skilled in the art will recognize other sing- and double-sided embodiments (see, for example, Collmen et al. (1993) *Science* 261:1404).

The synthesis schemes for metallosalenates which may be useful in the present method, or precursors thereof, can be adapted from the literature. For example, see Zhang et al. (1990) *J Am Chem Soc* 112:2801; Zhang et al. (1991) *J Org Chem* 56:2296; Jacobsen et al. (1991) *J Am Chem Soc* 113:7063; Jocobsen et al. (1991) *J Am Chem Soc* 113:6703; Lee et al. (1991) *Tetrahedron Lett* 32:5055; Jocobsen, E. N. In *Catalytic Asymmetric Synthesis*, Ojima, I. Ed., VCH: New York, 1993, chapter 4.2; E. N. Jacobsen PCT Publication WO81/14694 and WO93/03838; Larrow et al. (1994) *J Am Chem Soc* 116:12129; Larrow et al. (1994) *J Org Chem* 59:1939; Irie et al. (1990) *Tetrahedron Lett* 31:7345; Irie et al. (1991) *Synlett* 265; Irie et al. (1991) *Tetrahedron Lett* 32:1056; Irie et al. (1991) *Tetrahedron Asymmetry* 2:481; Katuski eta l. U.S. Pat. No. 5,352,814; Collman et al. (1993) *Science* 261:1404; Sasaki et al. (1994) *Tetrahedron* 50:11827; Palucki et al. (1992) *Tetrahedron Lett* 33:7111; and Srinivasan et al. (1986) *J Am Chem Soc* 108:2309.

Exemplary salenate ligands described in the above references are illustrated below, as well as in the appended examples [Ph=phenyl; tBu=tert-butyl].

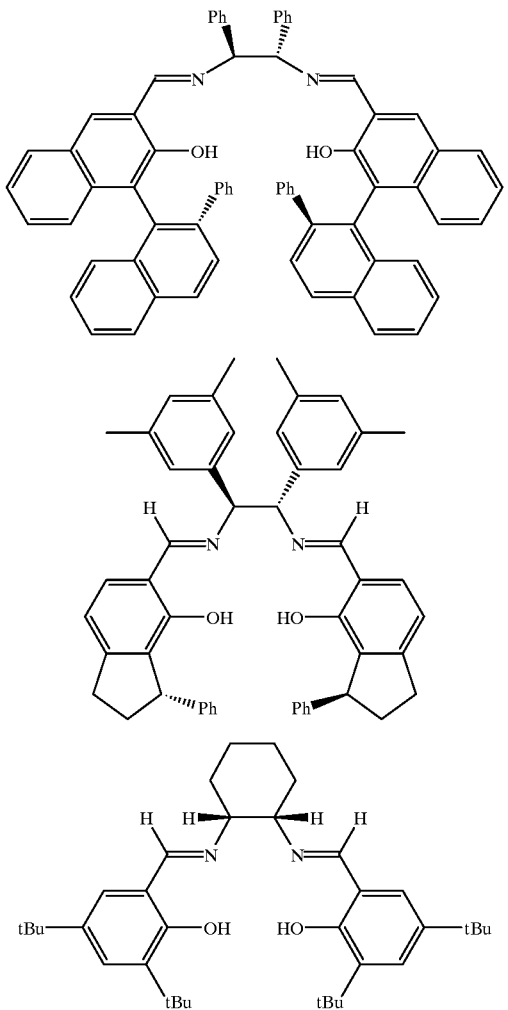

In yet another embodiment of the subject method, the tetradentate catalyst of formula 100 is derived as a chiral tetradentate ligand represented, with the metal atom, by the general formula:

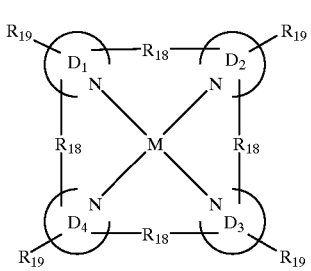

108 in which $D_1$, $D_2$, $D_3$ and $D_4$ each represent heterocycles, such as pyrrole, pyrrolidine, pyridine, piperidine, imidazole, pyrazine, or the like;

each $R_{18}$ occurring in the structure represents a bridging substituent which links adjacent heterocycles, and preferably contains at least one stereogenic center of the ligand. For example each $R_{18}$, represents an alkyl, an alkenyl, an alkynyl, or —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfonyl, a sulfur, a selenium, or an ester;

each $R_{19}$, independently, is absent or represents one or more substituents of the heterocycle to which it is attached, each substituent independently selected from the group consisting of halogens, alkyls, alkenyls, alkynyl, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, and —$(CH_2)_m$—$R_7$;

or any two or more of the $R_{18}$ and $R_{19}$ substituents are covalently linked to form a bridge substitution;

$R_7$ represents an aryl, a cycloalkyl, a cycloalkenyl, a heterocycle or a polycycle;

m is zero or an integer in the range of 1 to 8; and

M represents a transition metal, wherein each of the substituents $R_{18}$ and $R_{19}$ are selected such that the catalyst is asymmetric, e.g., the catalyst contains at least one stereogenic center. The metal will generally be coordinated with a counterion (as in the aged catalyst described below).

In preferred embodiment, $D_1$–$D_4$ are substituted pyrroles, and the catalyst is a chiral porphyrin or porphyrin-like ligand (hereinafter "porphyrinates"). As with the salenate ligands above, the synthesis of a vast number of porphyrinates has been reported in the literature. In general, most chiral porphyrins have been prepared in three ways. The most common approach involves attaching chiral units to preformed porphyrins such as amino- or hydroxy-substituted porphyrin derivatives (Groves et al. (1983) *J Am Chem Soc* 105:5891). Alternatively, chiral substituents can be introduced at the porphyrin-forming stage by allowing chiral aldehydes to condense with pyrrole (O'Malley et al. (1989) *J Am Chem Soc* 111:9116). Chiral porphyrins can also be prepared without the attachment of chiral groups. Similar to the bridged enantiotopic faces described for the salenates above, bridged porphyrinates can be generated by cross-linking adjacent and/or opposite pyrrolic positions and then separating the resulting mono-faced enantiomers with preparative HPLC using a chiral stationary phase (Konishi et al. (1992) *J Am Chem Soc* 114:1313). Ultimately, as with the generation of chiral salenate ligands, the resulting porphyrinate must have no mirror plane in order to be considered chiral.

With reference to formula 100, it will be understood that metalloporphyrinate catalysts, in addition to being represented by formula 108, can be represented generally by the compound of formula 100 when each of $Z_1$, $Z_2$, $Z_3$ and $Z_4$ represent nitrogen, and $C_1$ and $C_2$ along with their substituents (including $R_1$, $R'_1$, $R_2$, $R'_2$) form four substituted pyrrole rings which include $Z_1$, $Z_2$, $Z_3$ and $Z_4$. To complete the square tetradentate ligand, each pyrrole ring is covalently attached to the two adjacent pyrrole rings.

In preferred embodiments, the metalloporphyrinate catalyst is represented by the general formula:

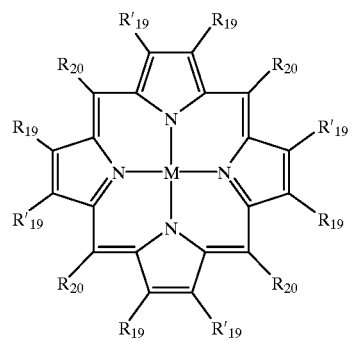

in which each $R_{20}$ occurring in structure 110, independently, represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, ester, or —$(CH_2)_m$—$R_7$;

each $R_{19}$ and $R'_{19}$ occurring in structure 110, independently, represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two $R_{19}$ and $R'_{19}$ substituents on the same pyrrole can be taken together to form a fused carbocycle or fused heterocycle having from 4 to 7 atoms in the ring structure;

or any two or more of the $R_{19}$, $R'_{19}$ and $R_{20}$ substituents are covalently cross-linked to form a bridging substituent;

$R_7$ represents an aryl, a cycloalkyl, a cycloalkenyl, a heterocycle or a polycycle;

m is zero or an integer in the range of 1 to 8; and

M represents a transition metal, wherein the substituents $R_{19}$, $R'_{19}$ and $R_{20}$ are selected such that the catalyst has at least one stereogenic center, e.g., is asymmetric. The metal will generally be coordinated with a counterion (as in the aged catalyst described below).

As with the salenate ligands previously described, it is possible to sterically and electronically "tune" the porphyrin ligands to optimize reaction yield and e.e. Examples of suitable porphyrin ligands and synthesis schemes can be adapted from the art. For example, see Chang et al. (1979) *J Am Chem Soc* 101:3413; Groves et al. (1989) *J Am Chem Soc* 111:8537; Groves et al. (1990) *J Org Chem* 55:3628; Mansuy et al. (1985) *J Chem Soc Chem Commun* p155; Nauta et al. (1991) *J Am Chem Soc* 113:6865; Collman et al. (1993) *J Am Chem Soc* 115:3834; and Kruper et al. (1995) *J Org Chem* 60:725.

Still another class of the tetradentate catalysts represented by the general formula 100 and which are useful in the present asymmetric synthesis reactions can be represented by the formula:

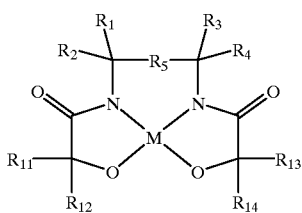

112 in which
  each of the substituents $R_1$, $R_2$, $R_3$, $R_4$, $R_5$, $R_{11}$, $R_{12}$, $R_{13}$ and $R_{14}$, independently, represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;
    or any two or more of the substituents taken together form a carbocycle or heterocycle having at least 4 atoms in the ring structure;
  $R_7$ represents an aryl, a cycloalkyl, a cycloalkenyl, a heterocycle or a polycycle;
  m is zero or an integer in the rang of 1 to 8; and
  M represents a transition metal;
wherein
  if $R_5$ is absent, at least one of $R_1$ and $R_2$ is covalently bonded to at least one of $R_3$ and $R_4$, and
  the substituents are selected such that the catalyst is asymmetric. The metal will generally be coordinated with a counterion (as in the aged catalyst described below).

Exemplary catalysts of formula 112 include:

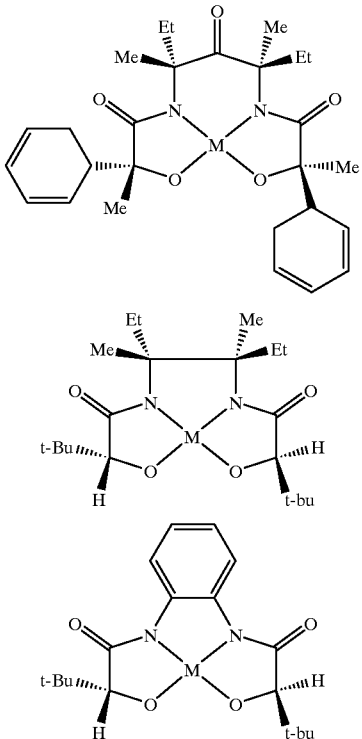

The synthesis of these and other related catalyst can be adapted from the literature. See, for example, Ozaki et al. (1990) *J Chem Soc Perkin Trans* 2:353; Collins et at. (1986) *J Am Chem Soc* 108:2088; and Brewer et al. (1988) *J Am Chem Soc* 110:423.

In yet another embodiment, the tetradentate catalysts of formula 100 can be chosen from the class of azamacrocycle having a ligand represented by the general formula:

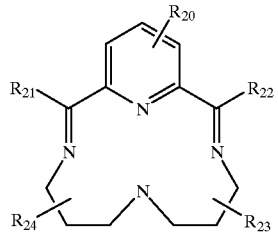

114 wherein $R_{21}$ and $R_{22}$ each represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{20}$ is absent or represents one or more substituents of the pyridine to which it is attached, each substituent independently selected from the group consisting of halogens, alkyls, alkenyls, alkynyls, hydroxyl, alkoxyl, sylyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{23}$ and $R_{24}$ each independently are absent or represent one or more substituents of the 1,3-diiminopropyl to which they are attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the $R_{20}$, $R_{21}$, $R_{22}$, $R_{23}$ $R_{24}$ substituents are covalently linked to form a bridging substituent;

$R_7$ represents an aryl, a cycloalkyl, a cycloalkenyl, a heterocycle or a polycycle; and m is zero or an integer in the range of 1 to 8;

wherein the substituent $R_{20}$, $R_{21}$, $R_{22}$, $R_{23}$ and $R_{24}$ are selected such that the catalyst is asymmetric.

One advantage to this class of tetradentate catalysts, like the salenates, derives from the fact that the ligand provides a metallo-shiff base complex. Furthermore, stereogenic centers can be sited within tow bond lengths of the metal center. Exemplary ligands of formula 114 include:

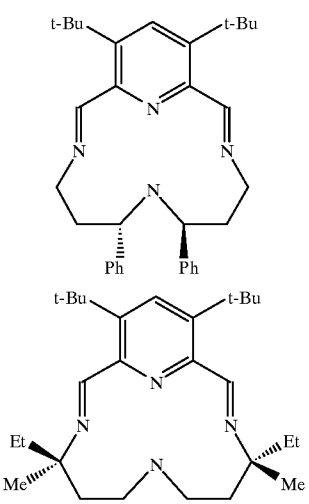

The synthesis of these and other embodiments of 114 are described in Prince et al. (1974) *Inorg Chim Acta* 9:51–54, and references cited therein.

Yet another class of tetradentate ligands of the subject method are the cyclams, such as represented by the general formula:

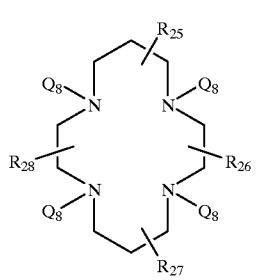

in which each of the substituents $Q_8$ independently, are absent or represent hydrogen or a lower alkyl, and each of $R_{25}$, $R_{26}$, $R_{27}$ and $R_{28}$, independently, represent one or more substituents on the ethyl or propyl diimine to which they are attached, which substituents are selected from the group of hydrogen, halogens, alkyls, alkenyls, alkynyls, hydroxyl, alkoxyl, silyloxy, amino, nitro, thiol, amines, imines, amides, phosphonates, phosphines, carbonyl, carboxyls, silyls, ethers, thioethers, sulfonyls, selenoethers, ketones, aldehydes, esters, and —$(CH_2)_m$—$R_7$; or any two or more of the substituents taken together form a bridging substituent; $R_7$ represents an aryl, a cycloalkyl, a cycloalkenyl, a heterocycle, or a polycycle; and m is zero or an integer in the range of 1 to 8. Wherein the substituents are selected such that the catalyst is asymmetric. Exemplary embodiments and synthesis schemes for chiral cyclams useful in the present invention can be adapted from the art. See, for example, the Burrows et al. U.S. Pat. No. 5,126,464, Kimura et al. (1984) *Inorg Chem* 23:4181; Kimura et al. (1984) *J Am Chem Soc* 106:5497; Kushi et al. (1985) *J Chem Soc Chem Commun* 216; Machida et al. (1986) *Inorg Chem* 25:3461; Kimura et al. (1988) *J Am Chem Soc* 110:3679; and Tabushi et al. (1977) *Tetrahedron Lett* 18:1049.

B. Chiral Tridentate Catalysts

In yet another embodiment of the subject method, the chiral catalyst which is provided in the reaction is from a class of chiral catalyst having a tridentate ligand which coordinates a transition metal in a substantially planar geometry, though as above some distortion to this geometry is contemplated. Accordingly, this planar geometry refers to tridentate ligands in which the Lewis basic atoms lie substantially in the same plane, with the metal also in that plane, or slightly above or below that plane.

Preferred planar tridentate catalysts which may be employed in the subject reactions can be represented by the general formula 140:

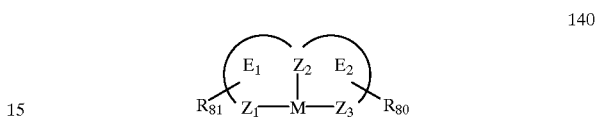

wherein $Z_1$, $Z_2$, and $Z_3$ each represent a Lewis base, such as selected from the group consisting of nitrogen, oxygen, phosphorus, arsenic and sulfur; the $E_1$ moiety, taken with $Z_1$, $Z_2$ and M, and the $E_2$ moiety, taken with $Z_2$, $Z_3$ and M, each, independently, from heterocycles; $R_{80}$ and $R_{81}$ each independently are absent, or represent one or more covalent substitutions of $E_1$ and $E_2$ with an organic or inorganic substituent permitted by valence requirements of the ring atom to which it is attached, or any two or more of the $R_{80}$ and $R_{81}$ substituents taken together form a briding substituent; and M represents a transition metal, wherein each $R_1$, $R_2$, $R'_1$, $R'_2$ $R_{80}$ and $R_{81}$ substituents are selected to provide at least one stereogenic center in said tridentate ligand. In preferred embodiments, each $R_{80}$ and $R_{81}$ occuring in 140 independently represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_7$ represents an aryl, a cycloalkyl, a cycloalkenyl, a heterocycle or a polycycle; and m is zero or an integer in the range of 1 to 8. The metal will generally be coordinated with a counterion (as in the aged catalyst described below).

For example, a chiral tridentate catalyst useful in the subject stereoselective reactions can have a ligand represented by the general formula:

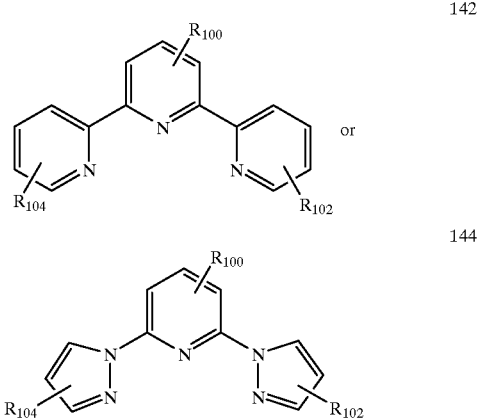

wherein each of $R_{100}$, $R_{102}$ and $R_{104}$ each independently are absent, or represent one or more covalent substitutions of heterocycle to which it is attached, or any two or more of the substituents taken together form a bridging substituent; wherein each $R_{100}$, $R_{102}$ and $R_{104}$ substituents, if present, can be selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_7$ represents an aryl, a cycloalkyl, a cycloalkenyl, a heterocycle or a polycycle; and m is zero or an integer in the range of 1 to 8. Again, the substitution of 142 is intended to provide at least one sterogenic center in the tridentate ligand. Exemplary embodiments of the 2,2':6', 2"-terpyridine ligands 142 and their synthesis can be adapted from, for example, Potts et al. (1987) *J Am Chem Soc* 109:3961; Hadda et al. (1988) *Polyhedron* 7:575; Potts et al. (1985) *Org Synth* 66:189; and Constable et al. (1988) *Inorg Chim Acta* 141:201. Exemplary 2,6-bis(N-pyrazolyl) pyridine ligands 144 can be adapted from, for example, Steel et al. (1983) *Inorg Chem* 22:1488; and Jameson et al. (1990) *J Org Chem* 55:4992.

Yet another class of planar tridentate catalyst useful in the subject stereoselective reactions can have a ligand represented by the general formula:

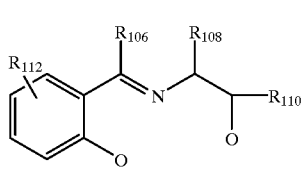

146 wherein each of $R_{106}$, $R_{108}$ and $R_{110}$ can be selected from the group consisting of hydrogens, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_{112}$ is absent or represent one or more covalent substitutions of the heterocycle to which it is attached; or any two or more of the $R_{106}$, $R_{108}$, $R_{110}$ and $R_{112}$ substituents taken together form a briding substituent; $R_7$ represents an aryl, a cycloalkyl, a cycloalkenyl, a heterocycle or a polycycle; and m is zero or an integer in the range of 1 to 8. The choice of substitution of 146 is intended to enhance its chirality. Exemplary embodiments of the salicylaldehyde-derived ligands 146 and their synthesis can be adapted from, for example, Desimoni et al. (1992) *Gazzetta Chimica Italiana* 122:269.

In a preferred embodiment, the tridentate ligand is given by the general formula 150

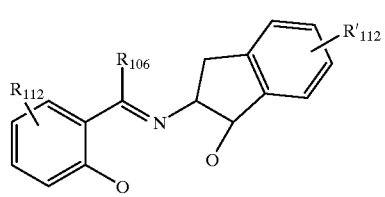

150 wherein $R_{106}$ represents a hydrogen, halogen, alkyl, alkenyl, alkynyl, hydroxyl, alkoxyl, silyloxy, amino, nitro, thiol amine, imine, amide, phosphonate, phosphine, carbonyl, carboxyl, silyl, ether, thioether, sulfonyl, selenoether, ketone, aldehyde, ester, or —$(CH_2)_m$—$R_7$; and each of $R_{112}$ and $R'_{112}$ is absent or represent one or more covalent substitutions of the heterocycle to which it is attached, such as designated for $R_{106}$; $R_7$ represents an aryl, a cycloalkyl, a cycloalkenyl, a heterocycle or a polycycle; and m is zero or an integer in the range of 1 to 8. For example, as described in the appended examples, a preferred salicyladehyde-derived ligand is given by the general formula 152

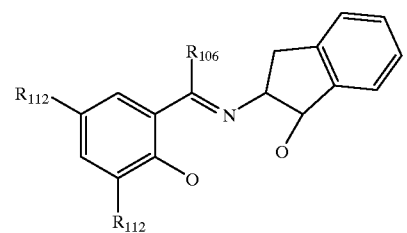

152 each $R_{112}$ being independently selected.

Still another class of planar tridentate catalyst useful in the subject steroselective reactions can have a ligand represented by the general formula:

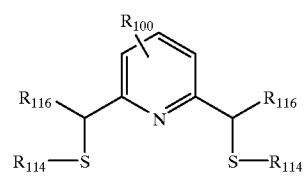

148 wherein $R_{100}$ is as described above, and each $R_{116}$ and $R_{114}$ can be selected from the group consisting of hydrogens, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; or any two or more of the substituents taken together form a bridging substituent; $R_7$ represents an aryl, a cycloalkyl, a cycloalkenyl, a heterocycle or a polycycle; and m is zero or an integer in the range of 1 to 8. The choice of substitution of 148 is intended to provide at least one sterogenic center in the tridentate ligand. Exemplary embodiments of the salicylaldehyde-derived ligands 148 and their synthesis can be adapted from, for example, Marangoni et al. (1993) *Polyhedron* 12:1669.

C. Tuning the Catalysts

The ligand substituents are chosen to optimize the selectivity of reaction and the catalyst stability. The exact mechanism of action of the metallosalenate-catalyzed cycladdition reactions has not yet been precisely elucidated. However, the need for stereoselective nonbonded interactions between the substrate and catalyst is a feature of this and other chiral planar catalysts of the subject reaction. While not wishing to be bound by any particular theory, it is believed that the present cycloaddition reactions involve two factors largely responsible for induction of asymmetry by formation of stereospecific nonbonded pairs of catalyst and substrate, namely, steric and electronic interactions between a substrate and the ligand of the chiral catalyst. In general, "tuning" refers altering the steric bulk of the ligand to limit the approach of the substrate, utilizing steric repulsions between the substrate and ligand substituents, and altering the electronic characteristics of the ligand to influence electronic interactions between the substrate and the ligand, as well as the rate and mechanism of the catalyzed reaction. For instance, the choice of appropriate substituents as "blocking groups" enforces certain approach geometries and disfavors others.

Furthermore, the choice of substituent may also affect catalyst stability; in general, bulkier substituents are found to provide higher catalyst turnover numbers. It has been found that for the asymmetric epoxidation of olefins by Mn(salen) complexes, t-butyl groups (or other tertiary groups) are suitable bulky moieties for optimizing steroeselectivity and increasing catalyst turnover.

A preferred embodiment for each of the embodiments described above provides a catalyst having a molecular weight less than 10,000 g/m (a.m.u.), more preferably less than 5000 g/m, and even more preferably less than 2500 g/m. In another preferred embodiment, none of the substituents of the core ligand, or any molecule coordinated to the metal in addition to the ligand, have molecular weights in excess 1000 g/m, more preferably they are less than 500 g/m, and even more preferably, are less than 250 g/m. The choice of substituent on the ligand can also be used to influence the solubility of the catalyst in a particular solvent system.

As mentioned briefly above, the choice of ligand substituents can also affect the electronic properties of the catalyst. Substitution of the ligand with electron-rich (electron-donating) moieties (including, for example, alkoxy or amino groups) increases the electron density of the ligand and at the metal center. Conversely, electron-withdrawing moieties (for example, chloro or trifluormethyl) on the ligand result in lower electron density of the ligand and metal center. The electron density of the ligand is important due to the possibility of interactions (such as $\pi$-stacking) with the substrate (see, e.g., Hamada et al. *Tetrahedron* (1994) 50:11827). The electron density at the metal center may influence the Lewis acidity of the metal. Choice of appropriate substituents thus makes possible the "tuning" of the reaction rate and the stereoselectivity of the reaction.

Substrates

Substrates which are useful in the present invention may be determined by the skilled artisan according to several criteria. In general, suitable substrates will have one or more of the following properties: 1) They will be capable of participating in a cycloaddition reaction under the subject conditions; 2) Said cycloaddition reaction will yield a useful product; 3) They will not react at undesired functionalities; 4) They will react at least partly through a mechanism catalyzed by the chiral catalyst; 5) They will not undergo significant further undesired reaction after reacting in the desired sense; 6) They will not substantially react with or degrade the catalyst, e.g. at a rate greater than conversion of the substrate. It will be understood that while undesirable side reactions (such as catalyst degradation) may occur, the rates of such reactions can be manipulated through the selection of reactants and conditions; these manipulations will render the undesired side reactions slow in comparison with the rate of the desired reaction(s).

In certain embodiments, the reactive substrates may be contained in the same molecule, thereby resulting in an intramolecular cycloaddition reaction.

As discussed above, a wide variety of substrates are useful in the methods of the present invention. The choice of substrates will depend on factors such as the desired product, and the appropriate substrates will be apparent to the skilled artisan. It will be understood that the substrates preferably will not contain any interfering functionalities. In general, appropriate substrates will contain either a reactive $\pi$-bond or a reactive 1,3-diene moiety.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the substrate, the catalyst, or the product. For example, the reaction temperature influences the speed of the reaction, as well as the stability of the reactants and catalyst. The reaction will usually be run at temperatures in the range of $-78°$ C. to $100°$ C., more preferably in the range $-20°$ C. to $50°$ C. and still more preferably in the range $-20°$ C. to $25°$ C.

In general, the asymmetric synthesis reactions of the present invention are carried out in a liquid reaction medium. The reactions may be run without addition of solvent (see Example 8, infra). Alternatively, the reactions may be run in an inert solvent, preferably one in which the reaction ingredients, including the catalyst, are substantially soluble. Suitable solvents include ethers such as diethyl ether, 1,2-dimethoxyethan, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed. In certain embodiments, ethereal solvents are preferred.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. The partial pressure of the reactive gas may be from 0.1 to 1000 atmospheres, more preferably from 0.5 to 100 atm, and most preferably from about 1 to about 10 atm. In certain embodiments it is preferably to perform the reactions under an atmosphere of an inert gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, derivativation with one or more of substituents of the ligand. The immobilized ligands can be complexed with the desired metal to form the chiral metallocatalyst. The catalyst, particularly the "aged" catalyst described herein (Example 8, infra), is easily recovered after the reaction as, for instance, by filtration or centrifugation.

Exemplification

The invention now being generally described, it will be more readily understood by reference to the following examples which are included merely for purposes of illustration of certain aspects and embodiments of the present invention, and are not intended to limit the invention.

The formal hetero-Diels-Alder reaction between 1-methoxy-3-[(trimethylsilyl)oxy]-1,3-butadiene (1, "Danishefsky's diene") and aldehydes provides useful access to dihydropyranones (2, eq. 1), a class of compounds with extensive utility in organic synthesis.[1] Recently, several groups have reported enantioselective catalytic versions of this reaction.[2] In most cases, these condensations have been shown not to involve a formal cycloaddition reaction, but rather to proceed via a Mukaiyama aldol condensation followed by cyclization under the influence of acid catalysis to generate 2.[2a,b] Recently we have found that chiral chromium- and cobalt-containing salen complexes catalyze the highly enantioselective reaction of nucleophiles with epoxides.[3] In an effort to ascertain whether other classes of nucleophile-electrophile reactions are promoted by such catalysts, we evaluated a series of chiral (salen)metal complexes for the hetero-Diels-Alder reaction shown in eq. 1, and identified that (salen)Cr(III)Cl complex 3 does indeed catalyze the reaction. Optimization of the catalyst and reaction conditions has led to the development of a protocol for this synthetically important transformation that requires only 2 mol % of readily available chiral catalyst and affords 2 with good enantioselectivity.

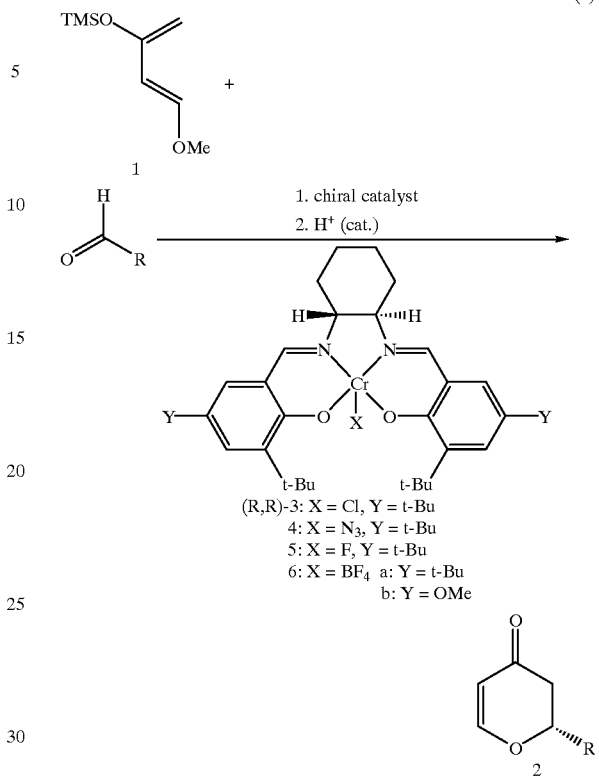

Results and Discussion

Several parameters were found to influence the rate and enantioselectivity of the condensation reaction. Reactions performed in non-coordinating ethereal solvents such as $Et_2O$ and TBME afforded the dihydropyranone in the highest yield and enantioselectivity. The reaction of 1 with benzaldehyde in the presence of 2 mol % (R,R)-3 at room temperature yielded R-2a in 96% isolated yield and 56% ee.[4] With an initial substrate concentration of 1.0 M, the reaction required 8 h to attain >90% conversion. At five-fold higher concentration the reaction was complete in 4 h with a slight increase in enantioselectivity (60% ee). A further increase to 64% ee was obtained with 68% isolated yield in reactions carried out at −30° C., although substantially longer reaction times were also required (70% conversion of 1 after 24 h with $[1]_0$=5 M).

The identity of the catalyst counterion was also revealed to be a critical parameter for the attainment of high enantioselectivity. For example, azide complex 4 displayed significantly higher enantioselectivity (81% ee) and yield (86%) at −30° C. relative to chloride catalyst 3 in the model reaction with benzaldehyde. Catalyst 5, bearing the more electronegative fluoride counterion, afforded even higher enantioselectivity (86% ee) although lower product yield (56%). Catalysts bearing less coordinating counterions $[X=BF_4, PF_6, B(Ar_f)_4(Ar_f=3,5-C_6H_3(CF_3)_2]$ proved to be much less reactive and less enantioselective. However, the addition of oven-dried powdered 4 Å molecular sieves to reactions with these catalysts led to increased yield and enantioselectivities in each case with the best result obtained with the tetrafluoroborate catalyst 6a, which afforded 2a in 87% ee and 85% isolated yield at −30° C. (Table 1, entry a). A brief screen of substitution of the salicylidene component of the salen ligand showed that catalyst 6a, derived from the commercially available t-butyl-substituted salen ligand, was the most effective although the methoxy-substituted catalyst 6b conferred measurably higher enantioselectivity and yield in select cases (entries e and f).

TABLE 1

Asymmetric Hetero-Diels-Alder Reactions of Diene 1 Catalyzed by 6a and 6b.[a]

| | | | cat 6a | | cat. 6b | |
|---|---|---|---|---|---|---|
| entry | R | temp (° C.) | ee (%)[b] | yield (%)[c] | ee (%)[b] | yield (%)[c] |
| a | Ph | −30 | 87 | 85 | 65 | 98 |
| b | $C_6H_{11}$ | −20 | 93 | 71 | 85 | 76 |
| c | n-$C_5H_{11}$ | −40 | 83 | 86 | 62 | 85 |
| d | 2-furyl | −10 | 76 (99) | 89 (63) | 68 | 80 |
| e | E-PhCH=CH | 0 | 70 | 65 | 73 (99) | 96 (64) |
| f | p-BrC$_6$H$_4$CH$_2$OCH$_2$ | −30 | 79 | 67 | 84 (99)[d] | 94 (70)[d] |
| g | o-ClC$_6$H$_4$CO$_2$CH$_2$ | −20 | 83 (99)[d] | 92 (67)[d] | 72 | 86 |

[a]Unless noted otherwise, all reactions were run at 5.0M in TBME using 2 mol % catalyst, 1.0 mmol of aldehyde, 1.0 mmol of diene 1, and 300 mg of oven dried 4Å molecular sieves for 24 h.
[b]Enantiomeric excesses in parentheses were obtained after recrystallization (see Experimental).
[c]Yields in parentheses refer to recrystallized yields.
[d]Reactions were run on 10.0 mmol scale.

The scope of the asymmetric condensation of 1 with aldehydes proved to be quite broad (Table 1). Although enantioselectivity in excess of 90% was achieved only in one case (entry b), several of the dihydropyranone products could be recrystallized to enantiomeric purity (entries d–g). The simplicity of the experimental procedure and the ready accessibility of the catalysts thus renders this an experimentally attractive method for the preparation of enantioenriched dihydropyranone derivatives.

An important question arises regarding the mechanism of the (salen)Cr-catalyzed condensation of 1 with aldehydes. A Mukaiyama aldol condensation mechanism has been identified in the highly effective asymmetric versions of this reaction developed by Keck and by Corey, whereas a concerted [4+2] cycloaddition pathway was indicated in the Eu(hfc)$_3$-catalyzed reaction reported by Danishefsky.[5] In the present (salen)Cr catalytic system, the $^1$H NMR spectrum of the crude reaction product of 1 with benzaldehyde catalyzed by complex 3 revealed the exclusive presence of cycloadduct 7 (eq. 2). To test the possible intermediacy of a Mukaiyama aldol condensation adduct, silyl ether 8 was synthesized independently[6] and subjected to the conditions of the Cr(salen)-catalyzed condensation reaction. However, no detectable cyclization of 8 to 7 was observed after exposure to 2 mol % of catalyst 3 for 6 h at room temperature. These results point toward a concerted [4+2] mechanism for the (salen)Cr catalysts, and thus extend the scope of enantioselective reactions catalyzed by these complexes to the important arena of cycloaddition chemistry.

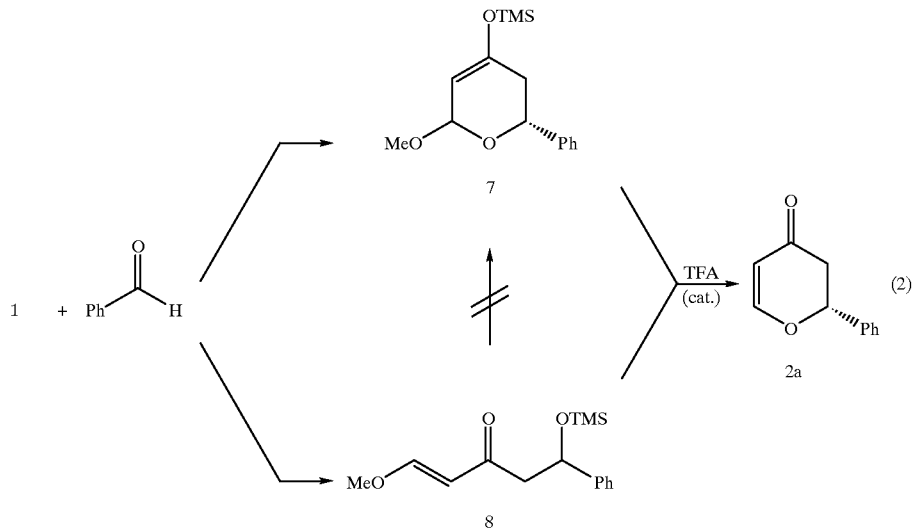

Experimental

Preparation of (R,R)-6a

To a solution of (R,R)-3 (632 mg, 1.00 mmol) in TBME (10 mL) was added AgBF$_4$ (195 mg, 1.00 mmol). The reaction flask was wrapped with aluminum foil and stirred at rt for 5 h after which it was filtered through Celite and washed with TBME. Evaporation of the solvent gave 680 mg (0.99 mmol, 99%) of a brown solid, which was used without further purification. IR (KBr, cm$^{-1}$) 2952, 1621, 1534, 1436, 1392, 1361, 1319, 1255, 1171, 1062; Exact mass (FAB) calcd for C$_{36}$H$_{52}$N$_2$O$_4$Cr[M-BF$_4$]$^+$: 596.3434; found: 596.3450.

Preparation of (R,R)-6b

Under a nitrogen atmosphere, $CrCl_2$ (86 mg, 0.70 mmol) was added to (R,R)-2,2'-[(1,2-cyclohexanediyl)bis(nitrilomethylidyne)]bis[4-methoxy-6-(1,1-dimethylethyl)phenol][7] (ligand of 6b, 285 mg, 0.580 mmol) in dry, degassed THF (10 mL). The resulting mixture was stirred under nitrogen for 3 h, at which time the flask was opened to air and allowed to stir for an additional 16 h at room temperature. The solution was diluted with TBME and rinsed with sat'd $NH_4Cl$ (5×50 mL) and sat'd NaCl (1×50 mL). The organic phase was separated, dried over $Na_2SO_4$, filtered, and concentrated in vacuo. The resulting residue was dissolved in TBME (7 mL) and treated with solid $AgBF_4$ (105 mg, 0.537 mmol). The reaction flask was wrapped with aluminum foil and stirred at rt for 5 h. The resulting mixture was filtered through Celite. Solvent removal by rotary evaporation afforded 328 mg (0.520 mmol, 90%) of 6b as a brown solid which was used without further purification. IR (KBr, $cm^{-1}$) 2949, 1623, 1546, 1459, 1422, 1345, 1313, 1175, 1062, 821; Exact mass (FAB) calcd for $C_{30}H_{40}N_2O_4Cr[M-BF_4]^+$: 544.2393; found: 544.2394.

Preparation of (R,R)-5

To a solution of (R,R)-6a (684 mg, 1.00 mmol) in acetonitrile (10 mL) was added NaF (84 mg, 2.00 mmol). The reaction mixture was stirred at room temperature for 24 h, solvent was removed by rotary evaporation, and the residue suspended in TBME and washed three times with water. The organic phase was dried, filtered through Celite, and evaporated to give 568 mg (0.92 mmol, 92% of 5 as a brown solid which was used without further purification. IR (KBr, $cm^{-1}$) 2964, 1623, 1533, 1463, 1392, 1361, 1321, 1256, 1170, 1083, 837; Exact mass (FAB) calcd for $C_{36}H_{52}N_2O_4Cr[M-F]^+$: 596.3434; found: 596.3423.

Representative Procedure for the Hetero-Diels-Alder Reaction of 1 with Aldehydes

(R)-2-Phenyl-2,3-dihydro-4H-pyran-4-one (2a)

A 10 mL oven dried flask equipped with a stir bar was charged with (R,R)-6a (13 mg, 0.02 mmol) and 0.3 g of oven dried powdered 4 Å molecular sieves. The flask was sealed with a rubber septum and purged with $N_2$. The catalyst was dissolved in TBME (200 µL) and benzaldehyde (100 µL, 1.0 mmol) was added via syringe at rt. The reaction was then cooled to −30° C. followed by the addition of 1-methoxy-3-[(trimethylsilyloxy]-butadiene (1) (195 µL, 1.0 mmol). The mixture was allowed to stir at −30° C. for 24 h at which time it was removed from the bath, diluted with 2 mL of $CH_2Cl_2$ and treated with a drop of TFA. After stirring 10 min at rt, the reaction was concentrated in vacuo and the crude residue was purified by flash chromatography (7:3 hexanes:EtOAc) to yield 2a[8] (151 mg, 0.85 mmol, 85% yield) as a clear oil. The isolated material was determined to be in 87% ee by chiral GC analysis (Cyclodex-B, 155° C., 20 min, isothermal, $t_R$(minor)=15.4 min, $t_R$(major)=15.7 min). $[\alpha]_D^{26}$ −96° (c 0.58, $CH_2Cl_2$); lit[2b] −83° for 82% ee material (c 0.5, $CHCl_3$).

(R)-2-Cyclohexyl-2,3-dihydro-4H-pyran-4-one (2b)

The crude product mixture was purified by flash chromatography (7:3 hexanes:EtOAc) to afford 2b in 71% yield (128 mg, 0.71 mmol) as a clear oil. The chromatographed material was determined to be in 93% ee by chiral GC analysis (Cyclodex-B, 150° C., isothermal, $t_R$(minor)=18.7 min, $t_R$(major)=19.3 min). $[\alpha]_D^{26}$ −157° (c 1.03, $CH_2Cl_2$); lit[2b] −159° for 76% ee material (c 0.5, $CHCl_3$); IR (thin film, $cm^{-1}$) 3498, 2927, 2856, 1677, 1595, 1450, 1408, 1276, 1225, 1038, 992, 910, 794; $^1H$ NMR ($CDCl_3$, 400 MHz) δ 7.36 (d, 2H, J=6.0 Hz), 5.38 (dd, 1H, J=1.0 and 6.0 Hz), 4.16 (ddd, 1H, J=3.3, 5.6 and 14.5 Hz), 2.54 (dd, 1H, J=14.5 and 16.7 Hz), 2.38 (ddd, 1H, J=1.0, 3.3 and 16.7 Hz), 1.64–1.81 (m, 6H), 1.00–1.27 (m, 5H); $^{13}C$ NMR ($CDCl_3$, 100 MHz) δ 193.3, 163.6, 106.9, 83.6, 41.4, 39.2, 28.2, 26.3, 25.9, 25.8; Exact mass (EI) calcd for $C_{11}H_{16}O_2[M]^+$: 180.1150; found: 180.1150. The absolute stereochemistry was assigned as (−)-R based on comparison of the measured rotation with the literature value.[2b]

(R)-2-Pentyl-2,3-dihydro-4H-pyran-4-one (2c)

Product 2c was obtained in 86% yield (145 mg, 0.86 mmol) as a clear oil after purification by flash chromatography (8:2 hexanes:EtOAc) and in 83% ee by chiral GC analysis (Cyclodex-B, 120° C., 21 min, 1° C./min to 130° C., $t_r$(minor)=24.5 min, $t_R$(major)=25.2 min). $[\alpha_D]^{26}$ −106° (c 0.500, $CH_2Cl_2$); IR (thin film, $cm^{-1}$) 2933, 1680, 1596, 1407, 1272, 1230, 1039, 897, 791; $^1H$ NMR ($CDCl_3$, 400 MHz) δ 7.36 (d, 2H, J=6.0 Hz), 5.40 (dd, 1H, J=1.1 and 6.0 Hz), 4.36–4.43 (m, 1H), 2.52 (dd, 1H, J=13.4 and 16.7 Hz), 2.42 (dt, 1H, J=2.8 and 12.8 Hz), 1.79–1.83 (m, 1H), 1.64–1.68 (m, 1H), 1.29–1.48 (m, 6H), 0.89 (t, 3H, J=7.0 Hz); $^{13}C$ NMR ($CDCl_3$, 100 MHz) δ 192.8, 163.3, 106.9, 79.6, 41.8, 34.3, 31.4, 24.4, 22.5, 13.9; Exact mass (EI) calcd for $C_{10}H_{16}O_2$ $[M]^+$: 168.1150; found: 168.1144. The absolute stereochemistry was assigned as (−)-R by analogy to compounds 2a,b,d.

(R)-2-(2-Furyl)-2,4-dihydro-4H-pyran-4-one (2d)

The crude product mixture was purified by flash chromatography (7:3 hexanes:EtOAc) to yield 2d[5a] in 89% yield (146 mg, 0.89 mmol) as a clear oil which solidified upon standing. The chromatographed material was determined to be 76% ee by chiral GC analysis (Cyclodex-B, 130° C., isothermal, $t_R$(minor)=20.5 min, $t_R$(major)=21.1 min). A single recrystallization from 1:2 $Et_2O$:hexanes yielded 103 mg (63%) of white needle-like crystals in 99% ee by GC analysis. $[\alpha]_D^{26}$ −357° (c 0.805, $CH_2Cl_2$); lit[2b] −255° for 67% ee material (c 0.5, $CHCl_3$).

(R)-2-E-Styryl-2,3-dihydro-4H-pyran-4-one (2e)

The crude residue obtained from the reaction was purified by flash chromatography (7:3 hexanes:EtOAc) to afford 2e[8] in 96% yield (191 mg, 0.96 mmol) as a clear oil which solidified after standing. The isolated material was determined to be 84% ee by chiral HPLC analysis (Chiralcel OD, 9:1 hexanes:IPA, 1.5 mL/min, $t_R$(minor)=11.2 min, $t_R$(major)=26.7 min). Recrystallization from a minimal amount of 4:1 $Et_2O$:hexanes at 0° C. yielded 128 mg (64%) of opaque needle like crystals in 99% ee by HPLC analysis. $[\alpha]_D^{26}$ −215° (c 0.36, $CH_2Cl_2$). The absolute stereochemistry was assigned as (−)-R by analogy to compounds 2a,b,d.

(R)-2-{[(4-Bromophenyl)methoxy]methyl}-2,3-dihydro-4H-pyran-4-one (2f)

Using 2.29 g (10.0 mmol) of [(4-bromophenyl)methoxy]acetaldehyde,[9] the crude residue from the reaction was purified by flash chromatography (7:3 hexanes:EtOAc) to yield 2f (2.81 g, 9.39 mmol, 94% yield) as a clear oil, which soldified upon standing, in 84% ee by chiral HPLC analysis (Chiralcel OD, 9:1 hexanes:IPA, 1 mL/min, $t_R$(minor)=11.3 min, t_R(major)=12.8 min). Recrystallization from a minimal amount of Et₂O at 0° C. yielded 2.09 g (70% of opaque cube like crystals in 99% ee by HPLC analysis. $[\alpha]_D^{26}$ −112° (c 1.74, CHCl₃); IR (Kbr, cm⁻¹) 2852, 1674, 1662, 1590, 1487, 1410, 1291, 1227, 1129, 1093, 1041, 890, 786; ¹H NMR (CDCl₃, 400 MHz) δ 7.48 (d, 2H, J=8.3 Hz), 7.37 (d, 1H, J=6.0 Hz), 7.21 (d, 2H, J=8.3 Hz), 5.42 (d, 1H, J=6.0 Hz), 4.56–4.62 (m, 3H), 3.66–3.74 (m, 2H), 2.74 (dd, 1H, J=14.2 and 16.8 Hz), 2.40 (dd, 1H, J=3.4 and 16.8 Hz); ¹³C NMR (CDCl₃, 100 MHz) δ192.3, 162.8, 136.5, 131.6, 129.3, 121.8, 107.2, 107.1, 78.2, 72.8, 70.8, 38.3; Exact mass (CI) calcd for C₁₃H₁₇BrNO₃ (M+NH₄)⁺: 314.0392; found: 314.0390. The absolute stereochemistry was assigned as (−)-R by analogy to compounds 2a,b,d.

(R)-2-{[(2-Chlorobenzoyl)oxy]methyl}-2,3-dihydro-4H-pyran-4-one (2g)

Using 1.99 g (10.0 mmol) of [(2-chlorobenzoyl)oxy]acetaldehyde,¹⁰ the crude residue from the reaction was purified by flash chromatography (7:3 hexanes:EtOAc) to yield 2g (2.44 g, 9.20 mmol, 92% yield) as a clear oil which solidified upon standing. The chromatographed material was determined to be 83% ee by chiral HPLC analysis (Chiralcel OD, 9:1 hexanes:IPA, 1 mL/min, t_R(minor)=20.6 min, t_R(major)=23.4 min). Recrystallization from a minimal amount of Et₂O at 0° C. yielded 1.78 g (67%) of opaque white crystals that were 99% ee by HPLC analysis. $[\alpha]_D^{26}$ −144° (c 0.508, CHCl₃); IR (KBr, cm⁻¹) 3068, 2958, 1740, 1681, 1592, 1407, 1298, 1270, 1215, 1141, 1123, 1055, 1041, 1028, 977, 872, 799; ¹H NMR (CDCl₃, 400 MHz) δ 7.84 (d, 2H, J=6.0 Hz), 7.2–7.5 (m, 4H), 5.45 (dd, 1H, J=0.9 and 6.0 Hz), 4.76 (m, 1H), 4.60 (dd, 1H, J=3.4 and 12.2 Hz), 4.53 (dd, 1H, J=5.6 and 12.2 Hz) 2.78 (dd, 1H, J=14.0 and 17.6 Hz), 2.53 (ddd, 1H, J=0.9, 3.6 and 17.6 Hz); ¹³C NMR (CDCl₃, 100 MHz) δ 190.9, 165.0, 162.5, 133.8, 133.0, 131.6, 131.2, 129.1, 126.6, 107.3, 76.6, 65.2, 38.2; Exact mass (CI) calcd for C₁₃H₁₁ClO₄[M]⁺: 266.0346; found: 266.0346. The absolute stereochemistry was assigned as (−)-R by analogy to compounds 2a,b,d.

References for Example (1) For reviews see: (a) Danishefsky, S. J. *Chemtracts* 1989, 273. (b) Danishefsky, S. J.; De Ninno, M. P. *Angew. Chem., Int. Ed. Engl.* 1987, 26, 15. (c) Danishefsky, S. J. *Aldrich. Acta.* 1986, 19, 59.
(2) (a) Keck, G. E.; Li, X. Y.; Krishnamurthy, D. *J. Org. Chem.* 1995, 60, 5998. (b) Corey, E. J.; Cywin, C. L.; Roper, T. D. *Tetrahedron Lett.* 1992, 33, 6907. (c) Ghosh, A. K.; Mathivanan, P.; Cappiello, J. *Tet. Lett.* 1997, 38, 2427. (d) Matsukawa, S.; Mikami, K. i Tetrahedron Asymm. 1997, 8, 815. (e) Gao, Q.; Maruyama, T.; Mouri, M.; Yamamoto, H. *J. Org. Chem.* 1992, 57, 1951. (f) Togni, A. *Organometallics* 1990, 9, 3106.
(3) (a) Martínez, L. E.; Leighton, J. L.; Carsten, D. H.; Jacobsen, E. N. *J. Am. Chem. Soc.* 1995, 117, 5897. (b) Larrow, J. F.; Schaus, S. E.; Jacobsen, E. N. *J. Am. Chem. Soc.* 1996, 118, 7420. (c) Jacobsen, E. N.; Kakiuchi, F.; Konsler, R. G.; Larrow, J. F.; Tokunaga, M. *Tetrahedron Lett.* 1997, 38, 773. (d) Tokunaga, M.; Larrow, J. F.; Kakiuchi, F.; Jacobsen, E. N. *Science* 1997, 277, 936.
(4) The absolute stereochemistry was assigned by comparison of the optical rotation with literature values (ref. 2a,b).
(5) (a) Bednarski, M.; Danishefsky, S. J. *J. Am. Chem. Soc.* 1983, 105, 3716. (b) Bednarski, M.; Danishefsky, S. J. *J. Am. Chem. Soc.* 1983, 105, 6968. (c) Bednarski, M.; Maring, C; Danishefsky, S. J. *Tetrahedron Lett.* 1983, 23, 3451.
(6) Compound 8 was prepared independently by the reaction of 1 with benzaldehyde in the presence of BF₃.OEt₂. Danishefsky, S. J.; Larson, E.; Askin, D.; Kato, N. *J. Am. Chem. Soc.* 1985, 107, 1246.
(7) Pospisil, P. J.; Carsten, D. H.; Jacobsen, E. N. *Chem. Eur. J.* 1996, 2, 974.
(8) Sher, F.; Isidor, J. L.; Taneja, H. R.; Carlson, R. M. *Tetrahedron Lett.* 1973, 8, 577.
(9) Prepared by a procedure analogous to the one described for [(4-methoxyphenyl)methoxy]acetaldehyde in: England, P.; Chun, K. H.; Moran, E. J.; Armstrong, R. W.; *Tetrahedron Lett.* 1990, 31, 2669.
(10) Prepared by a procedure analogous to the one described for (4-chlorobenzoyl)oxy]acetaldehyde in: Hashiguchi, S.; Maeda, Y.; Kishimoto, S.; Ochiai, M. *Heterocycles* 1986, 24, 2273.

EXAMPLE 1

Preparation of (R,R)-1,2-Diphenyl-1,2-bis(3-tert-butylsalicylideamino)ethane

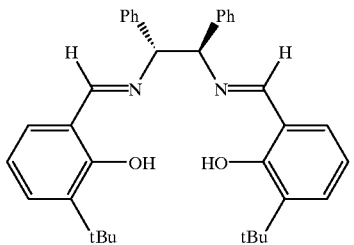

A solution of 360.5 mg (2.0 mmol) of 3-tert-butylsalicylaldehyde in 3 ml of EtOH was added dropwise to a solution of 212.3 mg (1.0 mmol) of (R,R)-1,2-diamino-1,2-diphenylethane in 5 ml of EtOH. The reaction mixture was heated to reflux for 1 h and water (5 ml) was added. The oil that separated solidified upon standing. Recrystallization from MeOH/H₂O gave 485.8 mg (91%) of yellow powder, mp 73–74° C. ¹H NMR (CDCl₃) δ 1.42 (s, 18H, CH₃), 4.72 (s, 2H, CHN=C), 6.67–7.27 (m, 16H, ArH), 8.35 (s, 2H, CH=N), 13.79 (s, 2H, ArOH) ppm; ¹³C NMR (CDCl₃) δ 29.3, 34.8, 80.1, 117.8, 118.5, 127.5, 128.0, 128.3, 129.6, 130.1, 137.1, 139.5, 160.2, 166.8 ppm. Anal. Calcd. for C₃₆H₄₀N₂O₂. C, 81.17; H, 7.57; N, 5.26. Found: C, 81.17; H, 7.60; N, 5.25.

EXAMPLE 2

Preparation of (R,R)-1,2-Diphenyl-1,2-bis(3-diphenylmethylsilylsalicylideamino)ethane

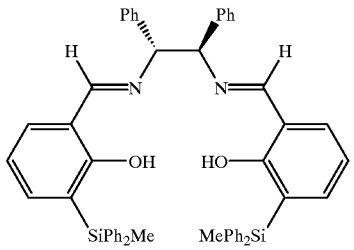

3-(Diphenylmethylsilyl)salicylaldehyde was prepared from 2-bromophenol in 5 steps according to established procedures. A solution of 348.3 mg (1.09 mmol) of 3-(diphenylmethylsilyl)salicylaldehyde and 116.0 mg (0.546 mmol) of (R,R)-1,2-diamino-1,2-diphenylethane in 5 ml of ethanol was heated to reflux for 0.5 h. A bright yellow oil separated from the solution and it solidified upon standing. The mixture was filtered and the yellow solid was washed with 2×5 ml ethanol. The isolated yield of product pure by $^1$H NMR analysis was 416 mg (97%). $^1$H NMR (CDCl$_3$) δ 0.95 (s, 3H), 4.68 (s, 2H), 6.72–7.55 (m, 36H, ArH), 8.37 (s, 2H), 13.34 (s, 2H) ppm.

EXAMPLE 3

Preparation 2,2'-Bis(3-tert-Butylsalicylideamino)-1,1'-Binaphthyl

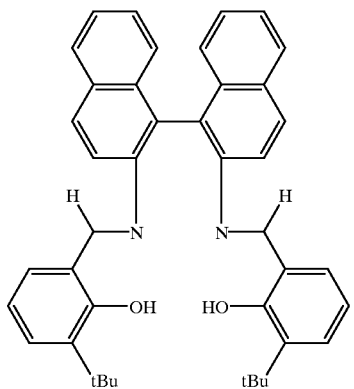

A solution of 725 mg (4.0 mmol) of 3-tert-butyl-salicylaldehyde in 6 ml of EtOH was added dropwise to a solution of 569 mg (2.0 mmol) of (+)-2,2'-diamino-1,1'-binaphthyl in 5 ml of EtOH. The reaction mixture was heated to reflux for 8 h and then volatile materials were removed under vacuum. The residue was purified by flash chromatography on 80 g SiO$_2$, using 20% CH$_2$Cl$_2$ in hexane as eluent. The mobile yellow fraction was collected and solvents were removed under vacuum to give 725 mg (1.20 mmol, 59% yield) of the diimine as a yellow powder.

EXAMPLE 4

Preparation of (S,S)-1,2,-bis(3,5-di-tert-butylsalicylide-amino)cyclohexane (2)

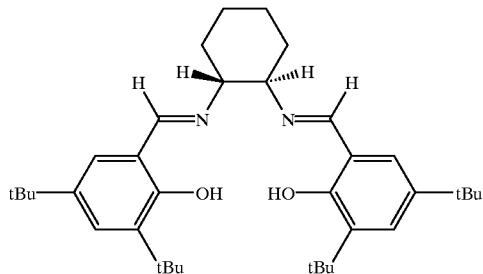

3,5-Di-t-butylsalicylaldehyde (2.0 equivalents) (prepared from the inexpensive, commercially available, 2,4-di-t-butylphenol according to Larrow, J. F.; Jacobsen, E. N.; Gao, Y.; Hong, Y.; Nie, X.; Zepp, C. M. *J. Org. Chem.* 1994, 59, 1939) was added as a solid to a 0.2 M solution of (S,S)-1,2-diaminocyclohexane (1.0 equivalent) (Aldrich Chemical Co., Milwaukee, Wis.) in absolute ethanol. The mixture was heated to reflux for 1 hr. and then H$_2$O was added dropwise to the cooled bright yellow solution. The resulting yellow crystalline solid was collected to filtration and washed with a small portion of 95% ethanol. The yield of analytically pure salen ligand 2 obtained in this manner was 90–97%.

Spectroscopic and analytical data for the salen ligand: $^1$H NMR (CDCl$_3$) δ 13.72 (s, 1H), 8.30 (S, 1H), 7.30 (d, J=2.3 Hz, 1H), 6.98 (d, J=2.3 Hz, 1H), 3.32 (m, 1H), 2.0–1.8 (m, 2H), 1.8–1.65 (m, 1H), 1.45 (m, 1H), 1.41 (s, 9H), 1.24 (s, 9H). $^{13}$C NMR (CDCl$_3$): δ 165.8, 158.0, 139.8, 136.3, 126.0, 117.8, 72.4, 34.9, 33.0, 31.4, 29.4, 24.3. Anal. Calcd. for C$_{36}$H$_{54}$N$_2$O$_2$: C, 79.07; H, 9.95; N, 5.12. Found: C, 79.12; H, 9.97; N, 5.12.

EXAMPLE 5

Preparation of (R,R)- and (S,S)-[1,2-bis(3,5-di-tert-butylsalicylideamino)cyclohexane]manganese(III) chloride The salen ligand synthesized in Example 4 is redissolved in hot absolute ethanol to give a 0.1 M solution. Solid Mn(OAc)$_2$.4H$_2$O(2.5 equivalents) is added in one portion and the solution is refluxed for 1 hr. Approximately 5 equivalents of solid LiCl are then added and the mixture is heated to reflux for an additional 0.5 hr. Cooling the mixture to 0° C. and addition of a volume of water equal to the volume of the brown ethanolic solution affords the Mn(III) complex as a dark brown powder which is washed thoroughly with H$_2$O, and isolated by filtration in 81–93% yield. Acceptable C, H, N, Cl and Mn analyses of the catalyst have been obtained (±0.4%), but these vary according to the extent of water and ethanol incorporation in the powdery product. The solvent content of the catalyst does not influence its effectiveness.

Analytical data for this catalyst: Anal. Calcd for C$_{36}$H$_{52}$ClMnN$_2$O$_2$.C$_2$H$_5$OH: C, 67.19; H, 8.31; Cl, 5.22; Mn, 8.09; N, 4.12: Observed: C, 67.05; H, 8.34; Cl, 5.48; Mn, 8.31; N, 4.28.

EXAMPLE 6

Preparation of (R,R)-[1,2-bis(3,5-di-tert-butylsalicylideamino)cyclohexane]chromium(III) chloride ((R,R)-1)

The following procedure was found to provide 1 with reproducible catalytic activity. Under a nitrogen atmosphere, 0.309 g (2.52 mmol) of CrCl$_2$ (anhydrous, 99.9%, Alfa/Johnson Matthey) was added to the (R,R)-ligand 2 synthesized in Example 4 (1.25 g, 2.29 mmol) in dry, degassed THF (45 mL). The resulting dark brown solution was stirred under N$_2$ for 3 h and then in air for an additional 3 h. The solution was then diluted with 250 ml of t-butyl methyl ether and washed with satd. NH$_4$Cl (3×150 ml) and brine (3×150 ml). The organic phase was dried (Na$_2$SO$_4$) and solvent was removed under reduced pressure, affording 1.41 g (87% yield) of 1 as a brown solid which was >98% pure as determined by HPLC analysis (octadecyl reverse phase, 100% CH$_3$CN). This material was used in the ring opening reactions without further purification. Recrystallization from acetonitrile provided high quality orange-brown crystals with 63% recovery: mp 375–398° C. (dec). IR (KBr, cm$^{-1}$) 3610 (br), 3420 (br), 2951 (s), 2866, 1619 (s), 1531, 1434, 1390, 1321, 1255, 1170, 1030, 837, 785, 748, 563, 543. Anal. Calcd for C$_{38}$H$_{59}$N$_2$O$_4$CrCl 1•$^3$⁄$_2$H$_2$O.½THF: C, 65.64; H, 8.55; N, 4.03; Cr, 7.48; Cl, 5.10. Found: C, 65.72; H, 8.53; N, 4.04; Cr, 7.45; Cl, 5.15. MS (FD): m/z 631

([M]+). HRMS (FAB): m/z calcd for $[C_{36}H_{52}N_2O_2Cr]+([1-Cl]+)$596.3418, found 596.3434. $\mu_{eff}$=3.97 $\mu_B$.

Conductance ($CH_3CN$, 0.0045M) 0.57 $\Omega^{-1}$ $cm^2$ $mol^{-1}$.

EXAMPLE 14

Synthesis of Catalyst 200

A tridentate catalyst was synthesized as descibed below. To a solution of (S,S)-201 ((S,S)-1-amino-2-hydroxyindane) (0.857 g, 5.75 mmol) in 60 ml EtOH was added 202 (1.829 g, 5.75 mmol) under a nitrogen atmosphere. The resulting solution was refluxed under $N_2$ for 12 hours. The solution was then cooled to room temperature, and solvent was removed under reduced pressure. The concentrate was purified by recrystallization from hexane to give 2.15 g–2.46 g (83%–95 yield) of 203.

In a dry Schlenk flask under a nitrogen atmosphere, (S,S)-203 (0.765 g, 1.7 mmol) was dissolved in dry THF (30 ml). 2,6-lutidine (0.730 g, 6.81 mmol, distilled over $CaH_2$) was added to the flask, followed by 0.638 g (1.70 mmol) chromium (III) chloride:tetrahydrofuran complex (1:3, 97%, Aldrich). The resulting dark brown solution was stirred under $N_2$ for 12 hours. The solution was then diluted with 200 ml of t-butyl methyl ether and washed with saturated $NH_4Cl$ (4×150 ml) and brine (3×150 ml). the organic portion was dried over $Na_2SO_4$, and the solvent was removed under reduced pressure. Catalyst-200 (0.890 mg, 95% yield) was obtained as a dark brown solid.

In a dry Schlenk flask under a nitrogen atmosphere, 200 (0.653 g, 1.22 mmol) was dissolved in azidotrimethylsilane (3 ml). the reaction mixture was stirred under $N_2$ for 12 hours and was then concentrated under reduced pressure to remove excess azidotrimethylsilane and TMSCl, and the resulting Cr-$N_3$ azide catalyst 204 could be used without further purification.

EXAMPLE 18

Synthesis of a chiral porphyrin ligand

Pyrrole (1.0 equivalents) and salicylaldehyde (1.2 equivalents) are dissolved in propionic acid (1 liter/20 ml pyrrole) and the solution is refluxed for 30 minutes. The reaction mixture is allowed to cool to room temperature and stand for one day. The mixture is filtered and the product is recrystallized to yield 5,10,15,20-tetrakis(2'-hydroxyphenyl)porphyrin.

The above-named porphyrin is dissolved is dimethylformamide, cooled to 0° C., and treated with sodium hydride (4 equivalents). The mixture is stirred for 30 minutes, and then a solution of D-threitol 1,4-ditosylate (Aldrich Chemical Co.) in DMF is added slowly. When the addition is finished, the reaction mixture is stirred for 30 minutes more, then carefully quenched. The organic phase is washed with brine and the solvent is evaporated. The residue is purified by HPLC to yield the chiral porphyrin.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A process of stereoselective chemical synthesis which comprises reacting a dienophile and a 1,3-diene in the presence of a non-racemic chiral catalyst to produce a stereoisomerically enriched product, wherein said dienophile is represented by formula 119, said 1,3-diene is represented by formula 118, and said chiral catalyst consists of an asymmetric tetradentate ligand, a metal atom, wherein said metal atom is not titanium, and a counterion, said catalyst having a rectangular planar or rectangular pyrimidal geometry.

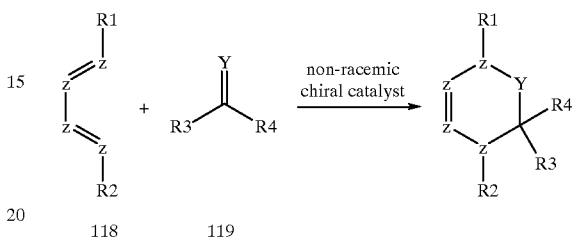

in which
   each occurrence of Z independently represents $C(R_{50})$, $Si(R_{50})$, N, or P, wherein $R_{50}$ represents a hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —$(CH_2)_m$—$R_7$;
   Y represents O, S, or $N(R_{50})$; and
   $R_1$, $R_2$, $R_3$, and $R_4$ represent independently for each occurrence hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —$(CH_2)_m$—$R_7$;
   $R_7$ represents an aryl, a cycloalkyl, a cycloalkenyl, a heterocycle or a polycycle; and
   m is zero or an integer in the range of 1 to 8.

2. The process of claim 1, wherein the metal atom is a transition metal from Groups 3–12 or from the lanthanide series.

3. The process of claim 1, wherein the metal atom is a late transition metal which is not in its highest state of oxidation.

4. The process of claim 2, wherein the metal atom is selected from the group consisting of Co, Cr, Mn, V, Fe, Mo, W, Ru and Ni.

5. The process of claim 1, wherein the catalyst is selected from the group consisting of chiral crown ethers complexed with a transition metal atom, the chiral catalyst represented by Formula 102,

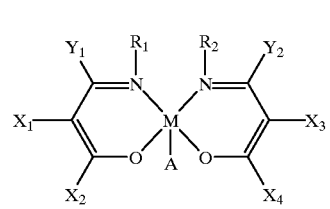

in which
   the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the substituents taken together form a carboxycle or heterocycle having from 4 to 8 atoms in the ring structure, which ring structure may be a fused ring, as in the case of, for example, $X_1$ and $X_2$ forming a ring, or which ring may be a bridging ring, as in the case of $R_1$ and $R_2$, $X_2$ and $X_4$, or $Y_1$ and $X_2$ representing different ends of a single substituent, with the proviso that at least one of $R_1$, $Y_1$, $X_1$ and $X_2$ is covalently bonded to at least one of $R_2$, $Y_2$, $X_3$ and $X_4$ to provide the β-iminocarbonyls as a tetradentate ligand;

$R_7$ represents an aryl, a cycloalkyl, cycloalkenyl, a heterocycle, or a polycycle;

m is zero or an integer in the range of 1 to 8;

M represents a transition metal;

A represents a counterion or a nucleophile; and the catalyst is asymmetric;

the chiral catalyst is represented by formula 108,

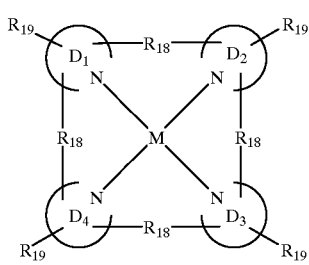

108 in which $D_1$, $D_2$, $D_3$ and $D_4$ each represent heterocycles, such as pyrrole, pyrrolidine, pyridine, piperidine, imidazole, pyrazine, or the like;

each $R_{18}$ occurring in the structure represents a bridging substituent which links adjacent heterocycles, and preferably contains at least one stereogenic center of the ligand. For example, each $R_{18}$, represents an alkyl, an alkenyl, an alkynyl, or -$R_{15}$-$R_{16}$-$R_{17}$-, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfonyl, a sulfer, a selenium, or an ester;

each $R_{19}$, independently, is absent or represents one or more substituents of the heterocycle to which it is attached, each substituent independently selected from the group consisting of halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, and —$(CH_2)_m$—$R_7$;

or any two or more of the $R_{18}$ and $R_{19}$ substituents are covalently linked to form a bridge substitution;

$R_7$ represents an aryl, a cycloalkyl, cycloalkenyl, a heterocycle or a polycycle;

m is zero or an integer in the range of 1 to 8;

M represents a transition metal; and the catalyst is asymmetric;

or the chiral catalyst is represented by formula 112,

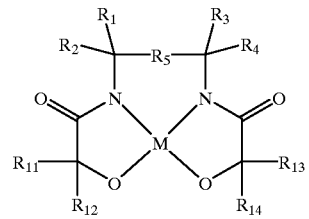

112 in which each of the substituents $R_1$, $R_2$, $R_3$, $R_4$, $R_5$, $R_{11}$, $R_{12}$, $R_{13}$ and $R_{14}$, independently, represent hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the substituents taken together form a carbocycle or heterocycle having at least 4 atoms in the ring structure;

$R_7$ represents an aryl, a cycloalkyl, cycloalkenyl, a heterocycle, or a polycycle;

m is zero or an integer in the range of 1 to 8; and

M represents a transition metal;

if $R_5$ is absent, at least one of $R_1$ and $R_2$ is covalently bonded to at least one of $R_3$ and $R_4$; and the catalyst is asymmetric;

or the chiral catalyst is represented by 114 and a complexed transition metal atom,

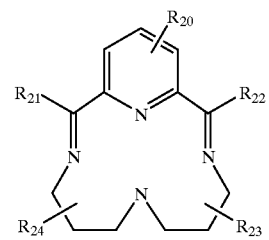

114 wherein $R_{21}$ and $R_{22}$ each represent hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{20}$ is absent or represents one or more substituents of the pyridine to which it is attached, each substituent independently selected from the group consisting of halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{23}$ and $R_{24}$ each independently are absent or represent one or more substituents of the 1,3-diiminopropyl to which they are attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$;

or any two or more of the R$_{20}$, R$_{21}$, R$_{22}$, R$_{23}$ and R$_{24}$ substituents are covalently linked to form a bridging substituent;

R$_7$ represents an aryl, a cycloalkyl, cycloalkenyl, a heterocycle or a polycycle; and m is zero or an integer in the range of 1 to 8; and the catalyst is asymmetric; and or the chiral catalyst is represented by 116 and a complexed transition metal atom,

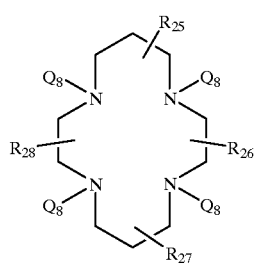

116 in which each of the substituents Q$_8$ independently, are absent or represent hydrogen or a lower alkyl;

each of R$_{25}$, R$_{26}$, R$_{27}$ and R$_{28}$, independently, represent one or more substituents on the ethyl or propyl diimine to which they are attached, which substituents are selected from the group of hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, and —(CH$_2$)$_m$—R$_7$; or any two or more of the substituents taken together form a bridging substituent;

R$_7$ represents an aryl, a cycloalkyl, a cycloalkenyl, a heterocycle, or a polycycle;

m is zero or an integer in the range of 1 to 8; and the ligand is asymmetric.

6. The process of claim 1, wherein the tetradentate ligand has at least one schiff base which complexes with the metal atom.

7. The process of claim 1, wherein the chiral catalyst has a molecular weight of less than 10,000 a.m.u.

8. The process of claim 1, wherein the substituents R$_1$, R$_2$, R$_3$, and R$_4$ each independently represent hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —(CH$_2$)$_m$—R$_7$;

or any two of the substituents R$_1$, R$_2$, and R$_{50}$, R$_3$, and R$_4$ taken together form a carbocylic or heterocyclic ring having from 4 to 8 atoms in the ring structure;

R$_7$ represents an aryl, a cycloalkyl, a cycloalkenyl, a heterocycle or a polycycle; and m is zero or an integer in the range of 1 to 8.

9. The process of claim 1, wherein either the 1,3-diene substrate, the dienophile substrate or both have a plane of symmetry.

10. The process of claim 1, wherein the dienophile substrate is selected from the group consisting of aldehydes, thioaldehydes, esters, thionesters, thioesters, dithioesters, amides, thioamides, lactones, thionolactones, thiolactones, dithiolactones, lactams, thiolactams, phosphorus ylides, ketones, thioketones, acid halides, anhydrides, imines, iminium ions, imines, oximes, oximes, hydrazones, nitroso-containing compounds, nitro-containing compounds, compounds containing a phosphorus-oxygen π-bond, and compounds containing a phosphorus-sulfur π-bond; and the 1,3-diene substrate is selected from the group consisting of substituted 1,3-butadienes, 1-aza-1,3-butadienes, 2-aza-1,3-butadienes, 1,2-diaza-1,3-butadienes, 1,3-diaza-1,3-butadienes, 1,4-diaza-1,3-butadienes, 2,3-diaza-1,3-butadienes, 1-phosphorous-1,3-butadienes, and 2-phosphorous-1,3-butadienes.

11. The process of claim 1, wherein the catalyst is immobilized on an insoluble matrix.

12. The process of claim 1, which process is an enantioselective reaction.

13. The process of claim 1, which process is a diastereoselective reaction.

14. The process of claim 13, which diastereoselective reaction is a kinetic resolution reaction.

15. A stereoselective cycloaddition process which comprises combining a dienophile and a 1,3-diene in the presence of a non-racemic chiral catalyst to produce a stereoisomerically enriched product, wherein said dienophile is represented by formula 119, said 1,3-diene is represented by formula 118, and said chiral catalyst consists of a chiral tetradentate ligand having at least one schiff base nitrogen, a transition metal atom, wherein said transition metal atom is not titanium, which is not in its highest state of oxidation, and a counterion;

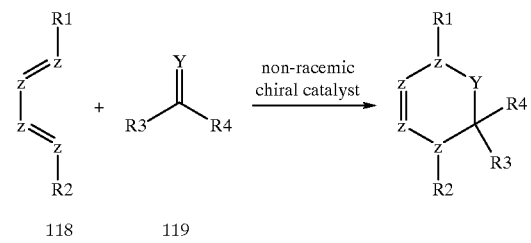

118    119 in which each occurrence of Z independently represents C(R$_{50}$), Si(R$_{50}$), N, or P, wherein R$_{50}$ represents a hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —(CH$_2$)$_m$—R$_7$;

Y represents O, S, or N(R$_{50}$); and

R$_1$, R$_2$, R$_3$, and R$_4$ represent independently for each occurrence hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —(CH$_2$)$_m$—R$_7$;

R$_7$ represents an aryl, a cycloalkyl, a cycloalkenyl, a heterocycle or a polycycle; and m is zero or an integer in the range of 1 to 8; and maintaining the combination under conditions whereby said chiral catalyst catalyzes a stereoselective cycloaddition reaction between said dienophile and said 1,3-diene.

16. The process of claim 15, wherein the metal is a selected from Group 5–12 transition metals.

17. The process of claim 15, wherein the metal is a Group 6 transition metal.

18. The process of claim 15, wherein the metal atom is selected from the group consisting of Co, Cr, Mn, V, Fe, Mo, W, Ru and Ni.

19. The process of claim 15, wherein the catalyst is represented by the general formula:

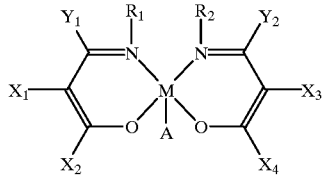

in which
the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;
or any two or more of the substituents taken together form a carbocycle or heterocycle ring having from 4 to 8 atoms in the ring structure,
with the proviso that at least one of $R_1$, $Y_1$, $X_1$ and $X_2$ is covalently bonded to at least one of $R_2$, $Y_2$, $X_3$ and $X_4$ to provide the β-iminocarbonyls to which they are attached as a tetradentate ligand, and at least one of $Y_1$ and $Y_2$ is a hydrogen;
$R_7$ represents an aryl, a cycloalkyl, a cycloalkenyl, a heterocycle, or a polycycle;
m is zero or an integer in the range of 1 to 8;
M represents the late transition metal; and
A represents a counterion or a nucleophile;
wherein the catalyst is asymmetric.

20. The process of claim 15, wherein the substituents $R_1$, $R_2$, $R_3$, and $R_4$ each independently represents hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —$(CH_2)_m$—$R_7$;
or any two of the substituents $R_1$, $R_2$, and $R_{50}$, or $R_3$, and $R_4$ taken together form a carbocylic or heterocyclic ring having from 4 to 8 atoms in the ring structure;
$R_7$ represents an aryl, a cycloalkyl, a cycloalkenyl, a heterocycle or a polycycle; and m is zero or an integer in the range of 1 to 8.

21. The process of claim 15, wherein either the 1,3-diene substrate, the dienophile substrate or both have a plane of symmetry.

22. The process of claim 15, wherein the dienophile substrate is selected from the group consisting of aldehydes, thioaldehydes, esters, thionesters, thioesters, dithioesters, amides, thioamides, lactones, thionolactones, thiolactones, dithiolactones, lactams, thiolactams, phosphorus ylides, ketones, thioketones, acid halides, anhydrides, imines, iminium ions, imines, oximes, oximes, hydrazones, nitroso-containing compounds, nitro-containing compounds, compounds containing a phosphorus-oxygen π-bond, and compounds containing a phosphorus-sulfur π-bond; and the 1,3-diene substrate is selected from the group consisting of substituted 1,3-butadienes, 1-aza-1,3-butadienes, 2-aza-1,3-butadienes, 1,2-diaza-1,3-butadienes, 1,3-diaza-1,3-butadienes, 1,4-diaza-1,3-butadienes, 2,3-diaza-1,3-butadienes, 1-phosphorous-1,3-butadienes, and 2-phosphorous-1,3-butadienes.

23. The process of claim 15, which process is an enantioselective cycloaddition.

24. The process of claim 15, which process is a diastereoselective cycloaddition.

25. The process of claim 24, which diastereoselective cycloaddition produces a kinetic resolution.

26. The process of claim 15, wherein the chiral catalyst has a molecular weight of less than 10,000 a.m.u.

27. A process of catalyzing a stereoselective cycloaddition reaction which comprises
combining a dienophile, a 1,3-diene, and a non-racemic chiral catalyst, wherein said dienophile is represented by formula 119, said 1,3-diene is represented by formula 118, and said chiral catalyst consists of a chiral tetradentate ligand, a transition metal atom, wherein said transition metal atom is not titanium, which is not in its highest state of oxidation, and a counterion;

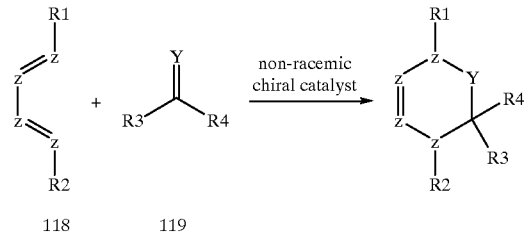

in which each occurrence of Z independently represents C($R_{50}$), Si($R_{50}$), N, or P, wherein $R_{50}$ represents a hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —$(CH_2)_m$—$R_7$;

Y represents O, S, or N($R_{50}$); and $R_1$, $R_2$, $R_3$, and $R_4$ represent independently for each occurrence hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —$(CH_2)_m$—$R_7$;

$R_7$ represents an aryl, a cycloalkyl, a cycloalkenyl, a heterocycle or a polycycle; and m is zero or an integer in the range of 1 to 8; and maintaining the combination under conditions whereby said chiral catalyst catalyzes a stereoselective cycloaddition reaction between said dienophile substrate and said 1,3-diene substrate.

28. The process of claim 27, wherein the chiral catalyst is represented by the general formula

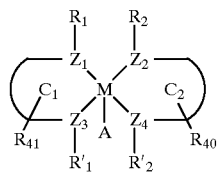

100 in which
Z₁, Z₂, Z₃ and Z₄ each represent a Lewis base;
the C₁ moiety, taken with Z₁, Z₃ and M, and the C₂ moiety, taken with Z₂, Z₄ and M, each, independently, form a heterocycle;
R₁, R₂, R'₁ and R'₂ each, independently, are absent or represent a covalent substitution with an organic or inorganic substituent permitted by valence requirements of the electron donor atom to which it is attached,
R₄₀ and R₄₁ each independently are absent, or represent one or more covalent substitutions of C₁ and C₂ with an organic or inorganic substituent permitted by valence requirements of the ring atom to which it is attached,
or any two or more of the R₁, R₂, R'₁, R'₂ R₄₀ and R₄₁ taken together form a bridging substituent;
with the proviso that C₁ is substituted at at least one site by R₁, R'₁ or R₄₁, and C₂ is substituted at at least one site by R₂, R'₂ or R₄₀, and
at least one of R₁, R'₁ and R₄₁ is taken together with at least one of R₂, R'₂ and R₄₀ to form a bridging substituent so as to provide Z₁, Z₂, Z₃ and Z₄ as a tetradentate;
M represents the late transition metal; and
A represents a counterion or a nucleophile,
wherein each R₁, R₂, R'₁, R'₂ R₄₀ and R₄₁ are selected to provide at least one stereogenic center in said tetradentate ligand.

29. The process of claim 28, wherein
R₁, R₂, R'₁ and R'₂, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH₂)ₘ—R₇;
each R₄₀ and R₄₁ occuring in formula 100 independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH₂)ₘ—R₇;
R₇ represents an aryl, a cycloalkyl, a cycloalkenyl, a heterocycle or a polycycle; and
m is zero or an integer in the range of 1 to 8.

30. The process of claim 28, wherein each Z₁, Z₂, Z₃ and Z₄ are independently selected from the group consisting of nitrogen, oxygen, phosphorus, arsenic, and sulfur.

31. The process of claim 28, wherein the M represents a late transition metal from one of the Group 5–12 transition metals.

32. The process of claim 27, wherein the metal atom is selected from the group consisting of Co, Cr, Mn, V, Fe, Mo, W, Ru and Ni.

33. The process of claim 28, wherein the M is Group 6 transition metal.

34. The process of claim 33, wherein the M is Cr(III).

35. The process of claim 27, wherein the catalyst is selected from the group consisting of chiral crown ethers complexed with a transition metal, the chiral catalyst is represented by 102,

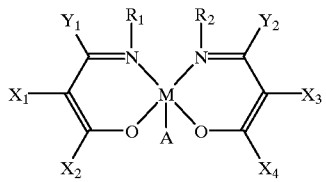

in which
the substituents R₁, R₂, Y₁, Y₂, X₁, X₂, X₃ and X₄ each, independently, represent hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —(CH₂)ₘ—R₇;
or any two or more of the substituents taken together form a carbocycle or heterocycle having from 4 to 8 atoms in the ring structure, which ring structure may be a fused ring, as in the case of, for example, X₁ and X₂ forming a ring, or which ring may be a bridging ring, as in the case of R₁ and R₂, X₂ and X₄, or Y₁ and X₂ representing different ends of a single substituent,
with the proviso that at least one of R₁, Y₁, X₁ and X₂ is covalently bonded to at least one of R₂, Y₂, X₃ and X₄ to provide the β-iminocarbonyls as a tetradentate ligand;
R₇ represents an aryl, a cycloalkyl, a cycloalkenyl, a heterocycle, or a polycycle;
m is zero or an integer in the range of 1 to 8;
M represents a transition metal;
A represents a counterion or a nucleophile; and
the catalyst is asymmetric;
or the chiral catalyst is represented by 108,

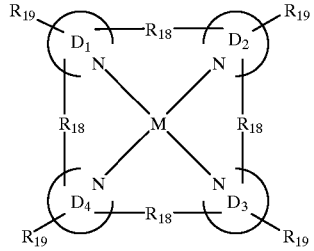

in which
D₁, D₂, D₃ and D₄ each represent heterocycles, such as pyrrole, pyrrolidine, pyridine, piperidine, imidazole, pyrazine, or the like;
each R₁₈ occurring in the structure represents a bridging substituent which links adjacent heterocycles, and preferably contains at least one stereogenic center of the ligand. For example, each R₁₈, represents an alkyl, an alkenyl, an alkynyl, or -$R_{15}$-$R_{16}$-$R_{17}$-, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfonyl, a sulfer, a selenium, or an ester;

each $R_{19}$, independently, is absent or represents one or more substituents of the heterocycle to which it is attached, each substituent independently selected from the group consisting of halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, and —$(CH_2)_m$—$R_7$;

or any two or more of the $R_{18}$ and $R_{19}$ substituents are covalently linked to form a bridge substitution;

$R_7$ represents an aryl, a cycloalkyl, cycloalkenyl, a heterocycle, or a polycycle;

m is zero or an integer in the range of 1 to 8;

M represents a transition metal; and the catalyst is asymmetric;

or the chiral catalyst is represented by 112,

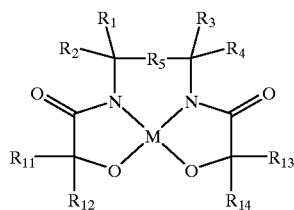

112 in which each of the substituents $R_1R_2$, $R_3$, $R_4$, $R_5$, $R_{11}$, $R_{12}$, $R_{13}$ and $R_{14}$, independently, represent hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the substituents taken together form a carbocycle or heterocycle having at least 4 atoms in the ring structure;

$R_7$ represents an aryl, a cycloalkyl, a cycloalkenyl, a heterocycle, or a polycycle;

m is zero or an integer in the range of 1 to 8; and

M represents a transition metal;

if $R_5$ is absent, at least one of $R_1$ and $R_2$ is covalently bonded to at least one of $R_3$ and $R_4$; and the catalyst is asymmetric;

or the chiral catalyst is represented by 114 and a complexed transition metal atom,

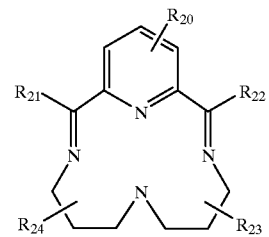

114 wherein $R_{21}$ and $R_{22}$ each represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{20}$ is absent or represents one or more substituents of the pyridine to which it is attached, each substituent independently selected from the group consisting of halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{23}$ and $R_{24}$ each independently are absent or represents one or more substituents of the 1,3-diiminopropyl to which they are attached, each substituent independently selected from the group consisting of halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the $R_{20}$, $R_{21}$, $R_{22}$, $R_{23}$ and $R_{24}$ substituents are covalently linked to form a bridging substituent;

$R_7$ represents an aryl, a cycloalkyl, a cycloalkenyl, a heterocycle, or a polycycle; and m is zero or an integer in the range of 1 to 8; and the ligand is asymmetric; and or the chiral catalyst is represented by 116 and a complexed transition metal atom,

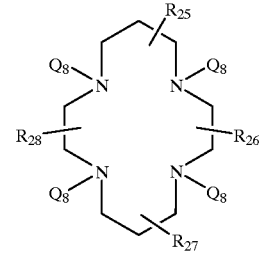

116 in which each of the substituents $Q_8$ independently, are absent or represent hydrogen or a lower alkyl;

each of $R_{25}$, $R_{26}$, $R_{27}$ and $R_{28}$, independently, represent one or more substituents on the ethyl or propyl diimine to which they are attached, which substituents are selected from the group of hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, and —$(CH_2)_m$—$R_7$; or any two or more of the substituents taken together form a bridging substituent;

$R_7$ represents an aryl, a cycloalkyl, a cycloalkenyl, a heterocycle, or a polycycle;

m is zero or an integer in the range of 1 to 8; and the ligand is asymmetric.

36. The process of claim 27, wherein the substituents $R_1$, $R_2$, $R_3$, and $R_4$ each independently represent hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —$(CH_2)_m$—$R_7$;

$R_7$ represents an aryl, a cycloalkyl, a cycloalkenyl, a heterocycle or a polycycle; and m is zero or an integer in the range of 1 to 8.

37. The process of claim 27, wherein either the 1,3-diene substrate, the dienophile substrate or both have a plane of symmetry.

38. The process of claim 27, wherein the dienophile substrate is selected from the group consisting of aldehydes, thioaldehydes, esters, thionesters, thioesters, dithioesters, amides, thioamides, lactones, thionolactones, thiolactones, dithiolactones, lactams, thiolactams, phosphorus ylides, ketones, thioketones, acid halides, anhydrides, imines, iminium ions, imines, oximes, oximes, hydrazones, nitroso-containing compounds, nitro-containing compounds, compounds containing a phosphorus-oxygen π-bond, and compounds containing a phosphorus-sulfur π-bond; and the 1,3-diene substrate is selected from the group consisting of substituted 1,3-butadienes, 1-aza-1,3-butadienes, 2-aza-1,3-butadienes, 1,2-diaza-1,3-butadienes, 1,3-diaza-1,3-butadienes, 1,4-diaza-1,3-butadienes, 2,3-diaza-1,3-butadienes, 1-phosphorous-1,3-butadienes, and 2-phosphorous-1,3-butadienes.

39. The process of claim 22, which process is an enantioselective cycloaddition.

40. The process of claim 22, which process is a diastereoselective cycloaddition.

41. The process of claim 40, which diastereoselective cycloaddition produces a kinetic resolution.

42. A process for synthesis of stereoisomerically enriched chiral compounds, comprising reacting a dienophile substrate with a 1,3-diene substrate in the presence of a chiral non-racemic catalyst, wherein said chiral catalyst catalyzes stereoselective cycloaddition between said dienophile substrate and said 1,3-diene substrate to produce a product which is stereoisomerically enriched, wherein the 1,3-diene and dienophile substrates are represented by general formulas 118, and 119, respectively;

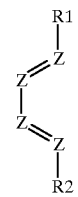

118

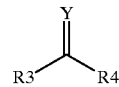

119 in which each occurrence of Z independently represents $C(R_{50})$, $Si(R_{50})$, N, or P, wherein $R_{50}$ represents a hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

Y represents O, S, or $N(R_{50})$; and $R_1$, $R_2$, $R_3$, and $R_4$ represent independently for each occurrence hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —$(CH_2)_m$—$R_7$;

the chiral catalyst is represented by the general formula:

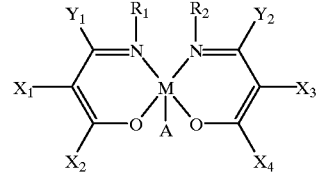

the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the substituents taken together form a carbocycle or heterocycle ring having from 4 to 8 atoms in the ring structure, with the proviso that at least one of $R_1$, $Y_1$, $X_1$ and $X_2$ is covalently bonded to at least one of $R_2$, $Y_2$, $X_3$ and $X_4$ to provide the α-iminocarbonyls to which they are attached as a tetradentate ligand, and at least one of $Y_1$ and $Y_2$ is a hydrogen;

$R_7$ represents an aryl, a cycloalkyl, a cycloalkenyl, a heterocycle or a polycycle;

m is zero or an integer in the range of 1 to 8;

M represents a transition metal atom, wherein said transition metal atom is not titanium; and A represents a counterion or a nucleophile, wherein the catalyst is asymmetric.

43. The process of claim 42, wherein the M represents a late transition metal selected from one of the Group 5–12 transition metals, which metal is not in its highest oxidation state.

44. The process of claim 43, wherein the metal atom is selected from the group consisting of Co, Cr, Mn, V, Fe, Mo, W, Ru and Ni.

45. The process of claim 42, wherein the M is a Group 6 transition metal.

46. The process of claim 45, wherein the M is Cr(III).

47. The process of claim 42, wherein the chiral, non-racemic catalyst is represented by the general formula 104:

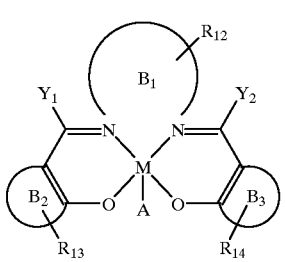

in which
  $B_1$ represents a diimine bridging substituent represented by -$R_{15}$-$R_{16}$-$R_{17}$-, wherein $R_{15}$ and $R_{17}$ each independently are absent or represent an alkyl, an alkenyl, or an alkynyl, and $R_{16}$ is absent or represents an amine, an imine, an amide, a phosphoryl, a carbonyl, a silyl, an oxygen, a sulfur, a sulfonyl, a selenium, a carbonyl, or an ester;
  each of $B_2$ and $B_3$ independently represent rings selected from a group consisting of cycloalkyls, cycloalkenyls, aryls, and heterocyclic rings, which rings comprising from 4 to 8 atoms in a ring structure;
  $Y_1$ and $Y_2$ each independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;
  $R_{12}$, $R_{13}$, and $R_{14}$ each independently are absent, or represent one or more covalent substitutions of $B_1$, $B_2$ and $B_3$ with halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$, wherein $R_{12}$ can occur on one or more positions of -$R_{15}$-$R_{16}$-$R_{17}$-,
  or any two or more of the $R_{12}$, $R_{13}$, $R_{14}$, $Y_1$ and $Y_2$ taken together form a bridging substituent;
  $R_7$ represents an aryl, a cycloalkyl, cycloalkenyl, a heterocycle, or a polycycle;
  m is zero or an integer in the range of 1 to 8;
  M represents a transition metal; and
  A represents a counterion or a nucleophile,
  wherein the catalyst is asymmetric.

48. The process of claim 42, wherein the substituents $R_1$, $R_2$, $R_3$, and $R_4$ each independently represent hydrogen, halogens, alkyls, alkenyls, alkynyls, hydroxyl, alkoxyl, silyoxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;
  or any two of the substituents $R_1$, $R_2$, and $R_{50}$, or $R_3$, and $R_4$ taken together form a carbocyclic or heterocyclic ring having from 4 to 8 atoms in the ring structure;
  $R_7$ represents an aryl, a cycloalkyl, a cycloalkenyl, a heterocycle or a polycycle; and m is zero or an integer in the range of 1 to 8.

49. The process of claim 42, wherein either the 1,3-diene substrate, the dienophile substrate or both have a plane of symmetry.

50. The process of claim 42, wherein the dienophile substrate is selected from the group consisting of aldehydes, thioaldehydes, esters, thionesters, thioesters, dithioesters, amides, thioamides, lactones, thionolactones, thiolactones, dithiolactones, lactams, thiolactams, phosphorus ylides, ketones, thioketones, acid halides, anhydrides, imines, iminium ions, imines, oximes, oximes, hydrazones, nitroso-containing compounds, nitro-containing compounds, compounds containing a phosphorus-oxygen π-bond, and compounds containing a phosphorus-sulfur π-bond; and the 1,3-diene substrate is selected from the group consisting of substituted 1,3-butadienes, 1-aza-1,3-butadienes, 2-aza-1,3-butadienes, 1,2-diaza-1,3-butadienes, 1,3-diaza-1,3-butadienes, 1,4-diaza-1,3-butadienes, 2,3-diaza-1,3-butadienes, 1-phosphorous-1,3-butadienes, and 2-phosphorous-1,3-butadienes.

51. The process of claim 42, which process is an enantioselective cycloaddition.

52. The process of claim 42, which process is a diastereoselective cycloaddition.

53. The process of claim 52, which diastereoselective cycloaddition produces a kinetic resolution.

54. A process of realizing a stereoselective cycloaddition between a dienophile substrate and a 1,3-diene wherein the 1,3-diene and dienophile substrates are represented by general formulas 118 and 119, respectively:

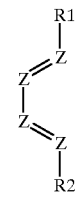

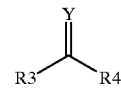

in which
  each occurrence of Z independently represents $C(R_{50})$, $Si(R_{50})$, N, or P, wherein $R_{50}$ represents a hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;
  Y represents O, S, or $N(R_{50})$; and
  $R_1$, $R_2$, $R_3$, and $R_4$ represent independently for each occurrence hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —$(CH_2)_m$—$R_7$;
  $R_7$ represents an aryl, a cycloalkyl, a cycloalkenyl, a heterocycle or a polycycle; and m is zero or an integer in the range of 1 to 8;
which method comprises reacting said dienophile with said 1,3-diene in the presence of at least a catalytic amount of a chiral metallosalenate catalyst, wherein said chiral metallosalenate catalyst does not comprise titanium.

55. The process of claim 54, wherein the metallosalenate catalyst is represented by the general formula:

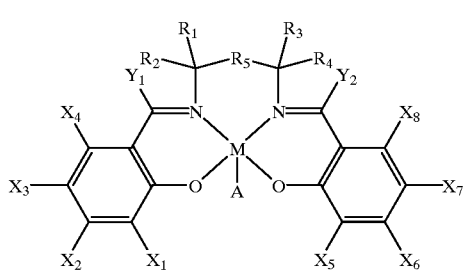

in which
each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;
or any two or more of the substituents taken together form a carbocycle or heterocycle having from 4 to 10 atoms in the ring structure;
$R_7$ represents an aryl, a cycloalkyl, a cycloalkenyl, a heterocycle, or a polycycle;
m is zero or an integer in the range of 1 to 8;
M represents a transition metal; and
A represents a counterion or a nucleophile;
wherein
if $R_5$ is absent, at least one of $R_1$ and $R_2$ is taken together with at least one of $R_3$ and $R_4$ to form a bridging substituent, and formula 106 is asymmetric.

56. The process of claim 54, wherein the substituents $R_1$, $R_2$, $R_3$, and $R_4$ each independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;
or any two of the substituents $R_1$, $R_2$, and $R_{50}$, or $R_3$, and $R_4$ taken together form a carbocylic or heterocyclic ring having from 4 to 8 atoms in the ring structure;
$R_7$ represents an aryl, a cycloalkyl, a cycloalkenyl, a heterocycle or a polycycle; and m is zero or an integer in the range of 1 to 8.

57. The process of claim 54, wherein either the 1,3-diene substrate, the dienophile substrate or both have a plane of symmetry.

58. The process of claim 54, wherein the dienophile substrate is selected from the group consisting of aldehydes, thioaldehydes, esters, thionesters, thioesters, dithioesters, amides, thioamides, lactones, thionolactones, thiolactones, dithiolactones, lactams, thiolactams, phosphorus ylides, ketones, thioketones, acid halides, anhydrides, imines, iminium ions, imines, oximes, oximes, hydrazones, nitroso-containing compounds, nitro-containing compounds, compounds containing a phosphorus-oxygen π-bond, and compounds containing a phosphorus-sulfur π-bond; and the 1,3-diene substrate is selected from the group consisting of substituted 1,3-butadienes, 1-aza-1,3-butadienes, 2-aza-1,3-butadienes, 1,2-diaza-1,3-butadienes, 1,3-diaza-1,3-butadienes, 1,4-diaza-1,3-butadienes, 2,3-diaza-1,3-butadienes, 1-phosphorous-1,3-butadienes, and 2-phosphorous-1,3-butadienes.

59. The process of claim 55, wherein the M represents a late transition metal from one of the Group 5–12 transitions metals.

60. The process of claim 59, wherein the metal atom is selected from the group consisting of Co, Cr, Mn, V, Fe, Mo, W, Ru and Ni.

61. The process of claim 55, wherein the M is a Group 6 transition metal.

62. The process of claim 61, wherein the M is Cr(III).

63. The process of claim 54, which process is an enantioselective cycloaddition.

64. The process of claim 54, which process is a diastereoselective cycloaddition.

65. The process of claim 64, which diastereoselective cycloaddition produces a kinetic resolution.

66. A process of resolving enantiomers from a racemic mixture of a chiral dienophile, or a racemic mixture of a chiral 1,3-diene having general formulas 118 and 119, respectively:

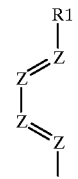

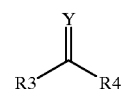

in which
each occurrence of Z independently represents $C(R_{50})$, $Si(R_{50})$, N, or P, wherein $R_{50}$ represents a hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;
Y represents O, S, or $N(R_{50})$; and
$R_7$ represents an aryl, a cycloalkyl, a cycloalkenyl, a heterocycle or a polycycle; and m is zero or an integer in the range of 1 to 8; and
$R_1$, $R_2$, $R_3$, and $R_4$ represent independently for each occurrence hydrogen, halogen, alkyl, alkenyl, alkynyl, hydroxyl, alkoxyl, silyloxy, amino, nitro, thiol, amine, imine, amide, phosphoryl, phosphonate, phosphine, carbonyl, carboxyl, silyl, ether, thioether, sulfonyl, selenoether, ketone, aldehyde, ester, or —$(CH_2)_m$—$R_7$;
the method comprising contacting said racemic mixture of the dienophile or 1,3-diene with an achiral 1,3-diene or dienophile, respectively, able to react with the racemic substrate in the presence of a chiral catalyst having the formula:

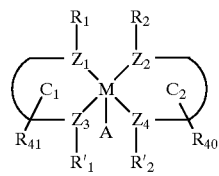

100 in which $Z_1$, $Z_2$, $Z_3$ and $Z_4$ each represent a Lewis base;

the $C_1$ moiety, taken with $Z_1$, $Z_3$ and M, and the $C_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached;

$R_{40}$ and $R_{41}$ each independently are absent or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$, $R_{40}$ and $R_{41}$ taken together form a bridging substituent, with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as a tetradentate;

M represents a transition metal, wherein said transition metal is not titanium; and A represents a counterion or a nucleophile, wherein each $R_1$, $R_2$, $R'_1$, $R'_2$, $R_{40}$ and $R_{41}$ are selected to provide at least one stereogenic center in said tetradentate ligand, under conditions wherein one enantiomer of the racemic dienophile or 1,3-diene reacts selectively in a cycloaddition with the achiral 1,3-diene or dienophile, respectively, leaving the other enantiomer of the racemic substrate substantially unchanged.

67. The process of claim 66, wherein $R_1$, $R_2$, $R'_1$ and $R'_2$, occurring in formula 100 independently, represent hydrogen, halogens, alkyls, alkenyls, alkynyls, hydroxyl, alkoxyl, silyloxy, amino, nitro, thiol amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

each $R_{40}$ and $R_{41}$ occurring in formula 100 independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

$R_7$ represents an aryl, a cycloalkenyl, a heterocycle or a polycycle; and m is zero or an integer in the range of 1 to 8.

68. The process of claim 66, wherein each $Z_1$, $Z_2$, $Z_3$ and $Z_4$ are independently selected from the group consisting of nitrogen, oxygen, phosphorus, arsenic, and sulfur.

69. A process of providing a non-racemic chiral dihydropyran, comprising reacting an aldehyde with a 1,3-diene in the presence of a chiral catalyst to produce a non-racemic chiral dihydropyran, wherein said chiral catalysts consists of an asymmetric tetradentate ligand, a metal atom, wherein said metal atom is not titanium, and a counterion, said chiral catalyst having a rectangular planar or rectangular pyrimidal geometry.

* * * * *